(12) United States Patent (10) Patent No.: US 7,914,437 B2
Gozzi et al. (45) Date of Patent: Mar. 29, 2011

(54) TRANSOBTURATOR METHODS FOR INSTALLING SLING TO TREAT INCONTINENCE, AND RELATED DEVICES

(75) Inventors: Christian Gozzi, Via Fiumes (IT); Peter Rehder, Igls (AT)

(73) Assignee: AMS Research Corporation, Minnetonka, MN (US)

( * ) Notice: Subject to any disclaimer, the term of this patent is extended or adjusted under 35 U.S.C. 154(b) by 1262 days.

(21) Appl. No.: 11/347,047

(22) Filed: Feb. 3, 2006

(65) Prior Publication Data

US 2006/0287571 A1 Dec. 21, 2006

Related U.S. Application Data

(60) Provisional application No. 60/734,238, filed on Nov. 7, 2005, provisional application No. 60/650,208, filed on Feb. 4, 2005, provisional application No. 60/650,209, filed on Feb. 4, 2005, provisional application No. 60/659,714, filed on Mar. 8, 2005, provisional application No. 60/659,504, filed on Mar. 8, 2005, provisional application No. 60/677,457, filed on May 4, 2005, provisional application No. 60/683,185, filed on May 20, 2005, provisional application No. 60/650,207, filed on Feb. 4, 2005.

(51) Int. Cl.
*A61F 2/00* (2006.01)
(52) U.S. Cl. ............................................. 600/29; 600/37
(58) Field of Classification Search ..................... 600/29, 600/30, 39, 143, 37
See application file for complete search history.

(56) References Cited

U.S. PATENT DOCUMENTS

| | | | |
|---|---|---|---|
| 4,827,940 A | | 5/1989 | Mayer et al. |
| 5,112,344 A | | 5/1992 | Petros |
| 5,531,783 A | | 7/1996 | Giele et al. |
| 5,611,515 A | | 3/1997 | Benderev et al. |
| 5,716,391 A | | 2/1998 | Grandjean |
| 5,842,478 A | | 12/1998 | Benderev et al. |
| 5,860,425 A | | 1/1999 | Benderev et al. |
| 5,899,909 A | | 5/1999 | Claren et al. |
| 6,039,686 A | * | 3/2000 | Kovac .............................. 600/30 |
| 6,042,534 A | | 3/2000 | Gellman et al. |
| 6,042,536 A | * | 3/2000 | Tihon et al. ..................... 600/37 |
| 6,110,101 A | | 8/2000 | Tihon et al. |
| 6,221,005 B1 | * | 4/2001 | Bruckner et al. ............... 600/30 |
| 6,273,852 B1 | | 8/2001 | Lehe et al. |
| 6,382,214 B1 | * | 5/2002 | Raz et al. ....................... 128/898 |
| 6,406,423 B1 | | 6/2002 | Scetbon |

(Continued)

FOREIGN PATENT DOCUMENTS

DE 20204669 9/2003

(Continued)

OTHER PUBLICATIONS de Leval J, Novel Surgical Technique for Treatment of Female Stress Urinary Incontinence: Transobturator Vaginal Tape Inside-Out. European Urology 44: 724-730, 2003.*

(Continued)

*Primary Examiner* — Charles A Marmor, II
*Assistant Examiner* — Catherine E. Burk
(74) *Attorney, Agent, or Firm* — Gregory L. Koeller; Kimberly K. Baxter

(57) ABSTRACT

Described are methods of treating urinary incontinence using a urinary sling and a tissue path that passes through the obturator foramen, along with related surgical implants, devices, systems, and kits.

31 Claims, 16 Drawing Sheets

U.S. PATENT DOCUMENTS

| | | |
|---|---|---|
| 6,475,139 B1 | 11/2002 | Miller |
| 6,478,727 B2 | 11/2002 | Scetbon |
| 6,575,897 B1 | 6/2003 | Ory et al. |
| 6,582,443 B2 | 6/2003 | Cabak et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,689,047 B2 | 2/2004 | Gellman |
| 6,691,711 B2 | 2/2004 | Raz et al. |
| 6,702,827 B1 | 3/2004 | Lund et al. |
| 6,755,781 B2 | 6/2004 | Gellman |
| 6,802,807 B2 | 10/2004 | Anderson et al. |
| 6,808,486 B1 | 10/2004 | O'Donnell |
| 6,884,212 B2 | 4/2005 | Thierfelder et al. |
| 6,908,425 B2 | 6/2005 | Luscombe |
| 6,911,002 B2 | 6/2005 | Fierro |
| 6,911,003 B2 | 6/2005 | Anderson et al. |
| 6,953,428 B2 | 10/2005 | Gellman et al. |
| 6,981,944 B2 | 1/2006 | Jamiolkowski et al. |
| 6,991,597 B2 | 1/2006 | Gellman et al. |
| 7,025,063 B2 | 4/2006 | Snitkin et al. |
| 7,037,255 B2 | 5/2006 | Inman et al. |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 * | 8/2006 | Tannhauser .................. 606/228 |
| 7,131,943 B2 * | 11/2006 | Kammerer ..................... 600/30 |
| 2001/0018549 A1 * | 8/2001 | Scetbon ......................... 600/30 |
| 2002/0099260 A1 * | 7/2002 | Suslian et al. ................. 600/30 |
| 2002/0143234 A1 * | 10/2002 | LoVuolo ........................ 600/30 |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0130670 A1 | 7/2003 | Anderson et al. |
| 2003/0176762 A1 * | 9/2003 | Kammerer ..................... 600/30 |
| 2003/0199732 A1 | 10/2003 | Suslian et al. |
| 2003/0212305 A1 * | 11/2003 | Anderson et al. ............. 600/29 |
| 2003/0220538 A1 * | 11/2003 | Jacquetin ...................... 600/37 |
| 2004/0006353 A1 | 1/2004 | Bosley, Jr. et al. |
| 2004/0087970 A1 | 5/2004 | Chu et al. |
| 2004/0106847 A1 * | 6/2004 | Benderev ...................... 600/37 |
| 2004/0193215 A1 | 9/2004 | Harari et al. |
| 2004/0230092 A1 | 11/2004 | Thierfelder et al. |
| 2004/0231678 A1 | 11/2004 | Fierro |
| 2004/0249240 A1 | 12/2004 | Goldmann et al. |
| 2005/0004424 A1 | 1/2005 | Raz et al. |
| 2005/0021086 A1 | 1/2005 | De Leval |
| 2005/0027220 A1 | 2/2005 | Wagner et al. |
| 2005/0038451 A1 | 2/2005 | Rao et al. |
| 2005/0038452 A1 | 2/2005 | Chu |
| 2005/0043580 A1 | 2/2005 | Watschke et al. |
| 2005/0065395 A1 | 3/2005 | Mellier |
| 2005/0075660 A1 | 4/2005 | Chu et al. |
| 2005/0080317 A1 | 4/2005 | Merade |
| 2005/0129733 A1 | 6/2005 | Milbocker et al. |
| 2005/0131274 A1 | 6/2005 | Suslian et al. |
| 2005/0143618 A1 | 6/2005 | Anderson et al. |
| 2005/0245787 A1 | 11/2005 | Cox et al. |
| 2005/0261545 A1 | 11/2005 | Gellman et al. |
| 2005/0267325 A1 | 12/2005 | Bouchier et al. |
| 2006/0009673 A1 | 1/2006 | Chan |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0235262 A1 | 10/2006 | Arnal |
| 2006/0247490 A1 | 11/2006 | Merade et al. |
| 2008/0076963 A1 * | 3/2008 | Goria ............................. 600/30 |

FOREIGN PATENT DOCUMENTS

| | | |
|---|---|---|
| EP | 1342450 | 9/2003 |
| EP | 1248567 | 3/2004 |
| EP | 1151722 | 8/2004 |
| WO | WO 98/35632 | 8/1998 |
| WO | WO 01/93656 | 12/2001 |
| WO | WO 02/39890 | 5/2002 |
| WO | WO 02/069781 | 9/2002 |
| WO | WO 2004/012579 | 2/2004 |
| WO | WO 2005/018494 | 3/2005 |

OTHER PUBLICATIONS

Rios L, Male Perineal Sling with Autologous Aponeurosis and Bone Fixation—Description of a Technical Modification. International Brazilian Journal of Urology 29(6): 524-527, Nov.-Dec. 2003.*

Palma P, Dambros M, Thiel M, Romano V, Griguol O, Riccetto C, and Netto N. Readjustable Transobturator Sling: A Novel Sling Procedure for Male Urinary Incontinence. Urologia Internationalis 73: 354-356, Mar. 25, 2004.*

John H. Bulbourethral Composite Suspension: A New Operative Technique for Post-Prostatectomy Incontinence. The Journal of Urology 171: 1866-1870, May 2004.*

Rios, Luis, A.S., Male Perineal Sling with Autologous Aponeurosis and Bone Fixation—Description of a Technical Modification, Int'l Braz. J. Urol. vol. 29 (6), 524-527 (Nov.-Dec. 2003).

Palina,."Readjustable Transobturator Sling, A Novel Sling Procedure for Male Urinary Incontinence," Urologia Internationalis, 73:354-356, Dec. 2004.

D. Dargent et al., Pose d'un ruban sous uretral oblique par voie obturatrice dans le traitement de l'incontinence urinaire feminine, Gynecol. Obstet. Fertil., 30: 576-582 (2002).

Moir J., et al., "The Gauze-Hammock Operation," The Journal of Obstetrics and Gynaecology of the British Commonwealth, vol. 75, No. 1, pp. 1-9, Jan. 1968.

Dietz et al., "Mechanical Properties of Urogynecologic Implant Materials," 14, 239-243 (2003).

Iglesia et al., "The Use of Mesh in Gynecologic Surgery," 8:105-115 (1997).

Bauer et al., The self-anchoring transobturator male sling to treat stress urinary incontinence in men: a new sling, a surgical approach and anatomical findings in a cadaveric study, BJU Int. vol. 95(9), pp. 1364-1366, 2005.

Pereya, "A Simplified Surgical Procedure for the Correction of Stress Incontinence in Women," West J. Surg., Obstetrics & Gynecology, pp. 223-226, Jul.-Aug. 1959.

Compression of the bulbar urethra by transobturator suburethral tape, Progres en Urologie, (abstract), 14(4) pp. 507-511, Sep. 2004.

* cited by examiner

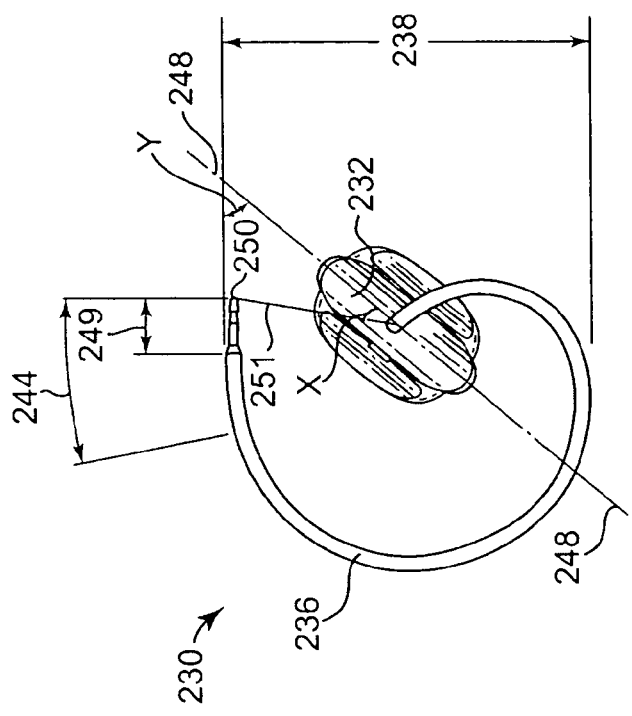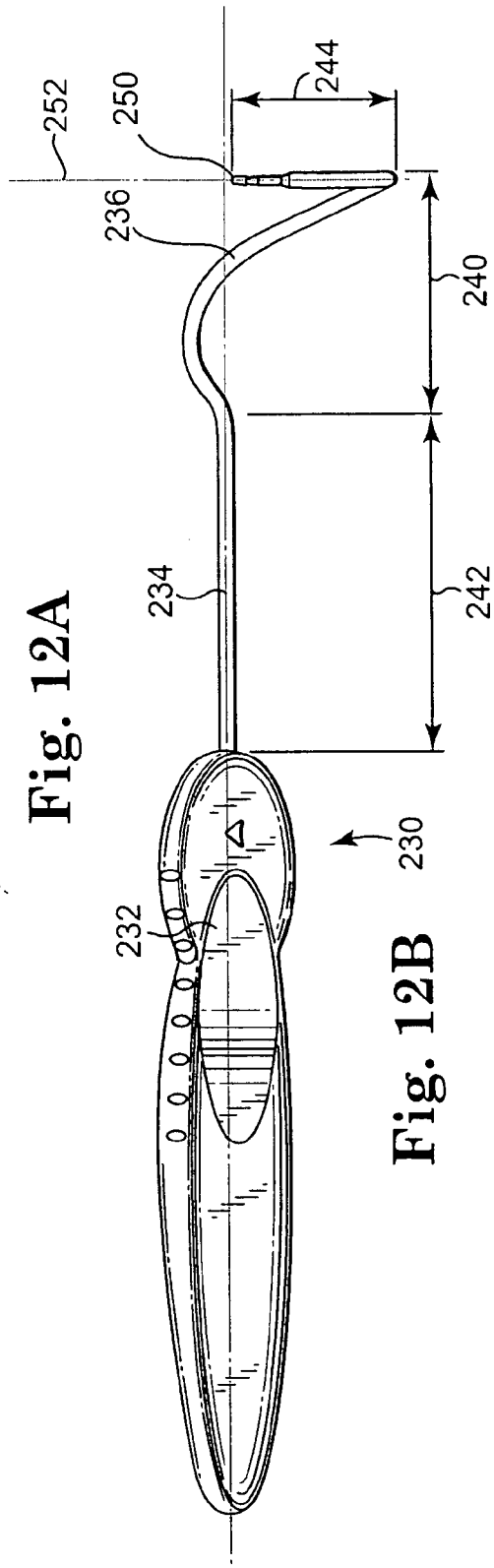
Fig. 12A
Fig. 12B

TRANSOBTURATOR METHODS FOR INSTALLING SLING TO TREAT INCONTINENCE, AND RELATED DEVICES

PRIORITY CLAIM

The present non-provisional patent application claims priority under 35 USC §119(e) from United States Provisional Patent Applications having U.S. Ser. No. 60/734,238, filed on Nov. 7, 2005, by Arnal et al., and titled TRANSOBTURATOR METHODS FOR INSTALLING SLING TO TREAT INCONTINENCE, AND RELATED DEVICES; U.S. Ser. No. 60/650,208, filed on Feb. 4, 2005, by Arnal et al., and titled TRANSOBTURATOR SLING FOR MEN; U.S. Ser. No. 60/650,209, filed on Feb. 4, 2005, by Arnal et al., titled TRANSOBTURATOR SLING FOR MEN; U.S. Ser. No. 60/659,714, filed on Mar. 8, 2005, by Arnal et al., titled NEEDLE DESIGN FOR MALE TRANSOBTURATOR SLING; U.S. Ser. No. 60/659,504, filed on Mar. 8, 2005, by Arnal, titled NEEDLE DESIGN IMPROVEMENTS FOR MALE TRANSOBTURATOR SLING; U.S. Ser. No. 60/677,457, filed on May 4, 2005, by Hauschild et al., titled URETHRAL SLING OF KNITTED MESH WITH EDGE TREATMENT; and U.S. Ser. No. 60/683,185, by Arnal, filed May 20, 2005, titled TRANSOBTURATOR SURGICAL SLING DELIVERY SYSTEM AND METHOD, and U.S. Ser. No. 60/650,207, filed on Feb. 4, 2005, by Rehder et al., titled TRANSOBTURATOR SLING FOR MEN, wherein the entirety of said provisional patent applications are incorporated herein by reference.

FIELD OF THE INVENTION

The invention relates to treating incontinence using a surgical sling, including methods, implants (e.g., slings), and delivery systems.

BACKGROUND

Men, women, and children of all ages can suffer from urinary incontinence or involuntary loss of urinary control. Their lives are perpetually interrupted by thoughts of ensuring that they have ready access to a restroom. Everyday activities such as attending a theater or sporting event can become unpleasant. Sufferers often begin to avoid social situations in an effort to reduce the stress associated with their condition.

A variety of treatment options are currently available. Some of these include external devices, behavioral therapy (such as biofeedback, electrical stimulation, or Kegel exercises), prosthetic devices, and surgery. Depending on the age, medical condition, and personal preference of a patient, surgical procedures can be used to completely restore continence.

One type of surgical procedure found to be an especially successful treatment option for incontinence in both men and women, is a sling procedure. Sling procedures typically entail surgically implanting a biocompatible implant or "sling" to support the bladder neck or urethra. Sling procedures are discussed in U.S. Pat. Nos. 5,112,344; 5,611,515; 5,842,478; 5,860,425; 5,899,909; 6,039,686; 6,042,534; 6,110,101; 6,478,727; 6,638,211; and PCT Publication Nos. WO 02/39890 and WO 02/069781.

Some "pubomedial" sling procedures involve an abdominal incision and installation of a sling between the rectus fascia in the abdominal region to a position below the urethra, and back again to the rectus fascia. A conventional procedure in females is to surgically place a sling by entering the abdominal cavity through an incision in the patient's pubovaginal region.

In males, one example of a conventional method involves surgical placement of a sling by entering the abdominal cavity through an abdominal incision. Unfortunately, to access the abdominal cavity a surgeon must incise the male patient's abdominal muscles. This procedure is more time consuming and uncomfortable for the male patient.

Other methods for treating pelvic conditions involve installation of a sling below the urethra through incisions made at the inner thigh (e.g., in the perineal skin facing the obturator and in the groin), and using a tissue path extending through the obturator. These procedures can be referred to as "transobturator" methods. See, e.g., U.S. Pat. No. 6,911,003 and Published U.S. Pat. Appl. No. 2003/0171644A1, the entireties of each being incorporated herein by reference.

While abdominal and transobturator methods of treating urinary incontinence can be effective, safe, and long-lasting, there is ongoing effort toward improving these methods.

SUMMARY

The invention relates to methods of treating urinary incontinence by surgical implantation of a urethral sling through a tissue path that traverses the obturator foramen. These "transobturator" methods generally involve two lateral incisions at the inner thigh, each near a patient's obturator foramen, and a third, medial incision at the perineum. An elongate sling is implanted between the medial incision and the two lateral incisions, with opposing end portions of the sling traversing each obturator foramen.

The sling can include two opposing elongate end portions that pass through each obturator foramen and a central support portion that is placed to support the urethra, below the urethra but not necessarily in contact with the urethra, as will be described. The central support portion can be adapted for contacting and supporting a pelvic tissue. According to exemplary embodiments, a central support portion of the sling can be placed in contact with tissue below the urethra such as the corpus spongiosum, and tensioned to support pelvic tissue including the urethra, to improve continence.

Exemplary embodiments of the inventive transobturator method can involve, generally speaking, implanting a urethral sling with end portions of the sling passing through the obturator, and with positioning and tensioning of a central support portion of the sling to approximate or support tissue of the pelvic region such as tissue of the urethra and related pelvic tissue. Continence can be improved by approximating pelvic tissue optionally to re-align or improve the alignment or positioning of the urethra relative to the rhabdosphincter. Desirably, the sling can be tensioned to approximate and lift the urethra (e.g., posterior urethra) proximally, toward the bladder, and place or return the urethra to an anatomically normal position, improving sphincter functioning, coaptation of the urethra, and continence.

According to preferred methods, a surgical installation involves a medial incision at the perineum that exposes the bulbospongiosus muscle (also known as the BC or bulbocavernosum muscle), dissection of the bulbospongiosus muscle tissue to expose the corpus spongiosum, and placement of the central support portion in contact with the corpus spongiosum. Optionally the central support portion can be attached to the corpus spongiosum, e.g., by suture or other fastening mechanism. Tension can be applied to the end portions of the sling to approximate the corpus spongiosum (CS), urethra (e.g., posterior urethra), and related tissues in a proximal direction toward the bladder.

A useful urethral sling can generally be of the type currently in use as an implanted surgical device for treating urinary incontinence, as well as similar slings developed in the future. Examples can be found in the patent literature such as at U.S. Pat. No. 6,911,003 and Published U.S. Pat. Appl. No. US 2003/0171644A1. Commercially available slings that could be useful with the techniques and methods described herein include the MONARC™ sling and implant system available from American Medical Systems, Inc., of Minnetonka Minn. Preferred urethral slings for placement at the corpus spongiosum can have a widened central support portion for a greater area of contact and greater amount of friction between the central support portion of the sling and the corpus spongiosum. Alternately or in addition, preferred implants can have reinforced end portions such as those described in Assignee's copending U.S. patent application Ser. No. 11/347,553, entitled "NEEDLE DESIGN FOR MALE TRANSOBTURATOR SLING," filed on even date herewith, and being incorporated herein by reference; and U.S. patent application Ser. No. 11/347,063, entitled "PELVIC IMPLANTS AND RELATED METHODS," filed on even date herewith, and being incorporated herein by reference; and U.S. patent application Ser. No. 11/347,596, entitled SURGICAL IMPLANTS AND RELATED METHODS AND SYSTEMS, filed on even date herewith, and being incorporated herein by reference.

The sling can be installed using one or more tools to manipulate the urethral sling to a desired position. Examples include curved two-dimensional or three-dimensional tools shaped to allow passage between the lateral incision and the medial incision. End portions of the implant can be connected to or associated with ends of the needles, one for installing an end portion between a left-side lateral incision and to the medial incision, through the obturator foramen. An opposing tool can assist to install the other end portion between the right-side lateral incision and the medial incision, through the obturator foramen. Examples of these types of tools are shown, e.g., at U.S. Pat. No. 6,911,003 and at Published U.S. Patent Application No. 2003/0171644A1. Optionally, a single tool may be used to install both sides of the sling through the left and right obturator foramen.

Exemplary left and right-handed tools can be designed with dimensions that are particularly suitable for installation of a sling using a transobturator method, in a male. These include relatively larger diameter and length of a three-dimensional portion, and a handle that provide an ergonomic advantage during a surgical installation procedure. These tools are described in Assignee's copending U.S. patent application Ser. No. 11/347,553, entitled "NEEDLE DESIGN FOR MALE TRANSOBTURATOR SLING," filed on even date herewith, and being incorporated herein by reference.

Also contemplated according to the invention are kits useful for commercial sale to surgeons, that include an implant and one or two installation tools adapted to install the implant using a transobturator method. The sling and the tool or tools can be specifically designed to be useful for a male transobturator method, in that the tools can be designed with specific features of strength, and the sling can exhibit properties of increased strength, increased area of contact between the central support portion and tissue, and increased short-term and long-term fixation upon installation.

In one aspect, the invention relates to a method of treating incontinence. The method includes: providing an elongate implantable sling comprising a central support portion and elongate end portions sized and shaped to extend between an incision substantially adjacent to a patient's obturator foramen, through the obturator foramen, and to a location below the urethra; creating a pair of lateral incisions substantially adjacent a patient's left and right obturator foramen; creating a medial incision at the perineum; exposing bulbospongiosus muscle; dissecting bulbospongiosus muscle to expose corpus spongiosum, placing the central support portion to contact the corpus spongiosum; and extending the end portions internally through the obturator foramen to the lateral incisions substantially adjacent to the obturator foramen.

In another aspect, the invention relates to a method of treating incontinence. The method includes installing a supportive sling below the bulbous urethra. Tension can be placed on the sling to approximate pelvic tissue including the urethra, to improve sphincter function and coaptation of the urethra.

BRIEF DESCRIPTION OF THE DRAWINGS

FIGS. 12A and 12B illustrate a tool useful according to the invention.

All figures are schematic and not necessarily to scale.

DETAILED DESCRIPTION

Surgical methods of the invention are methods of implanting a urethral sling ("sling") to treat urinary incontinence using a tissue path that passes through the obturator foramen. Embodiments of the invention relate to surgical techniques, implants, tools, and related systems, kits, and assemblies, generally useful for treating incontinence involving this transobturator technique. "Transobturator" methods generally involve two lateral incisions at the left and right inner thigh regions, each near a patient's obturator foramen, and a third, medial external incision at the perineum. The sling is installed between the medial incision and the two lateral incisions with a central support portion of the sling being placed below the urethra, to support the urethra, not necessarily in contact with the urethra itself but optionally and preferably in contact with tissue below the urethra. The sling is then tensioned to approximate pelvic tissue to improve continence.

The present invention treats incontinence in a way that is different from previous methods of treating incontinence in males. Past methods such as a retropubic urethral suspension using a sling, or installation of an artificial urinary sphincter ("AUS"), operate by a compressive effect on the sphincter that is meant to produce obstruction of the urethra. In contrast, the invention can be used to treat incontinence by re-positioning and approximating pelvic tissue in a way that improves or increase the efficiency with which pelvic tissues function to coapt the urethra, without requiring a compressive effect on the urethra itself.

According to the invention, a patient may suffer from pelvic tissue prolapse, weakness, or dislocation, due to one or more factors of age, weak and sagging perineal floor muscles, as a result of a surgical procedure to the prostate such as a partial or radical prostatectomy, or for any other reason. Pelvic tissue prolapse may be in the form of mis-positioning of one or more component pelvic tissue that makes up the urinary sphincter complex.

Within the general inventive concept of approximating pelvic tissue to treat incontinence, a urethral sling can be installed to approximate and support pelvic tissue, e.g., of the urethra, perineal body, urethral sphincter complex, etc., in any way that improves positioning of pelvic tissue to improve coaptation of the urethra, resulting in improved continence. According to one embodiment, a central support portion of a sling may be placed below the bulbospongiosus muscle and tensioned to re-position pelvic tissue and improve continence. In preferred embodiments, a urethral sling can be installed in a male patient with the central support portion of the sling in direct contact with the corpus spongiosum.

Figure 1:
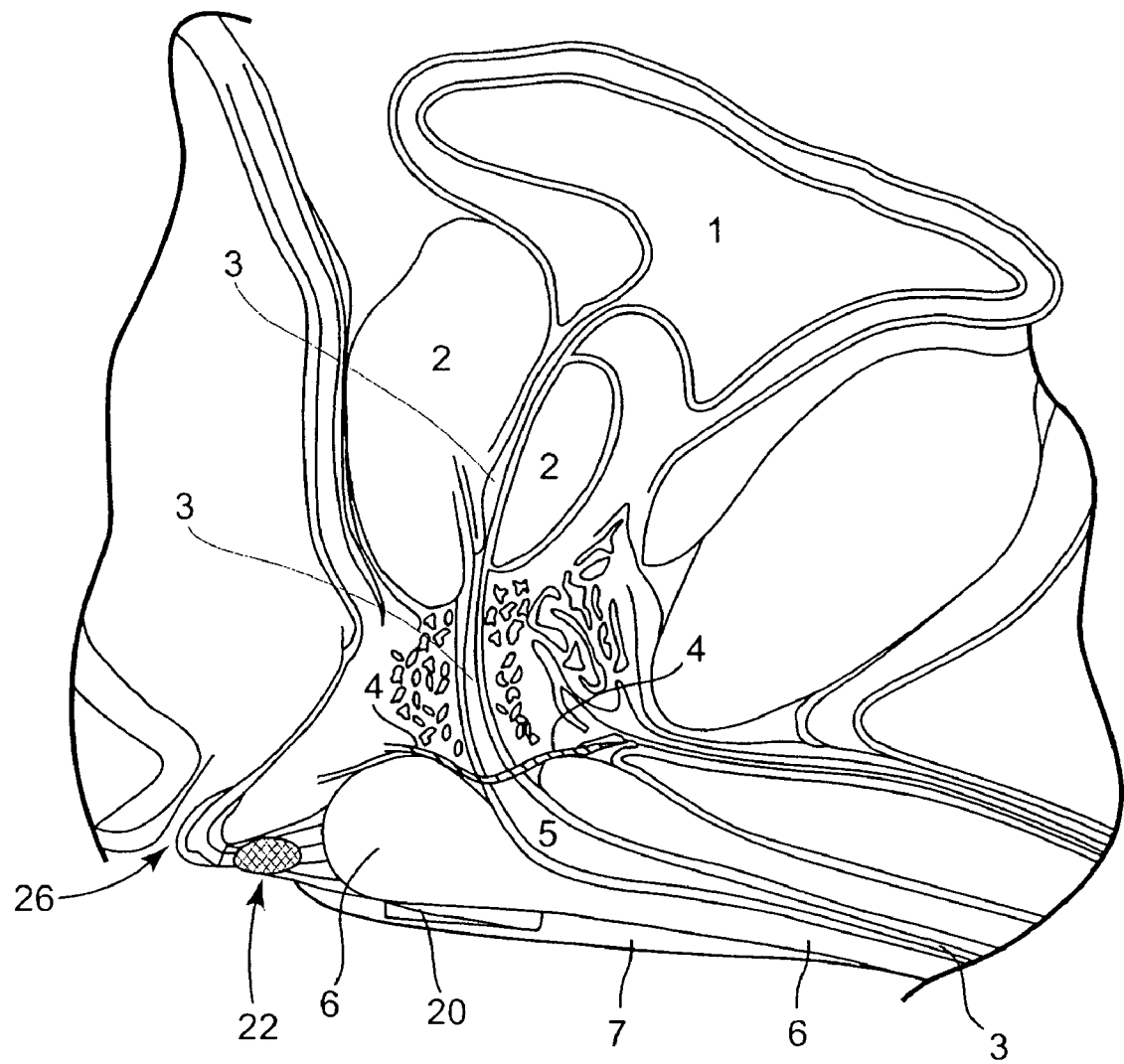
FIG. 1 illustrates general pelvic anatomy and a location of a urethral sling according to the invention.

Certain relevant pelvic anatomy is illustrated at FIG. 1, which shows tissue of the male pelvic cavity. Bladder 1 connects to a proximal end of urethra 3, at the bladder neck. Urethra 3 extends distally from bladder 1, through prostate 2 and below prostate 2, through perineal membrane 4 (the portion of the urethra associated with perineal membrane 4 can be referred to as the "membranous urethra"). Portion 5 of urethra 3 located distally relative to perineal membrane 4 is referred to as "bulbar urethra" 5. (As used herein, the terms "proximal" and "distal" as referring to portions of the urethra will be used to refer to positions toward the external orifice of the urethra as being "distal," and to refer to positions toward the bladder as "proximal.") Tissue below perineal membrane 4 and bulbar urethra 5 includes corpus spongiosum 6 and bulbospongiosus muscle 7. Central tendon 22 connects the posterior of corpus spongiosum 6 and bulbospongiosus muscle 7, adjacent to anus 26.

Figure 2:
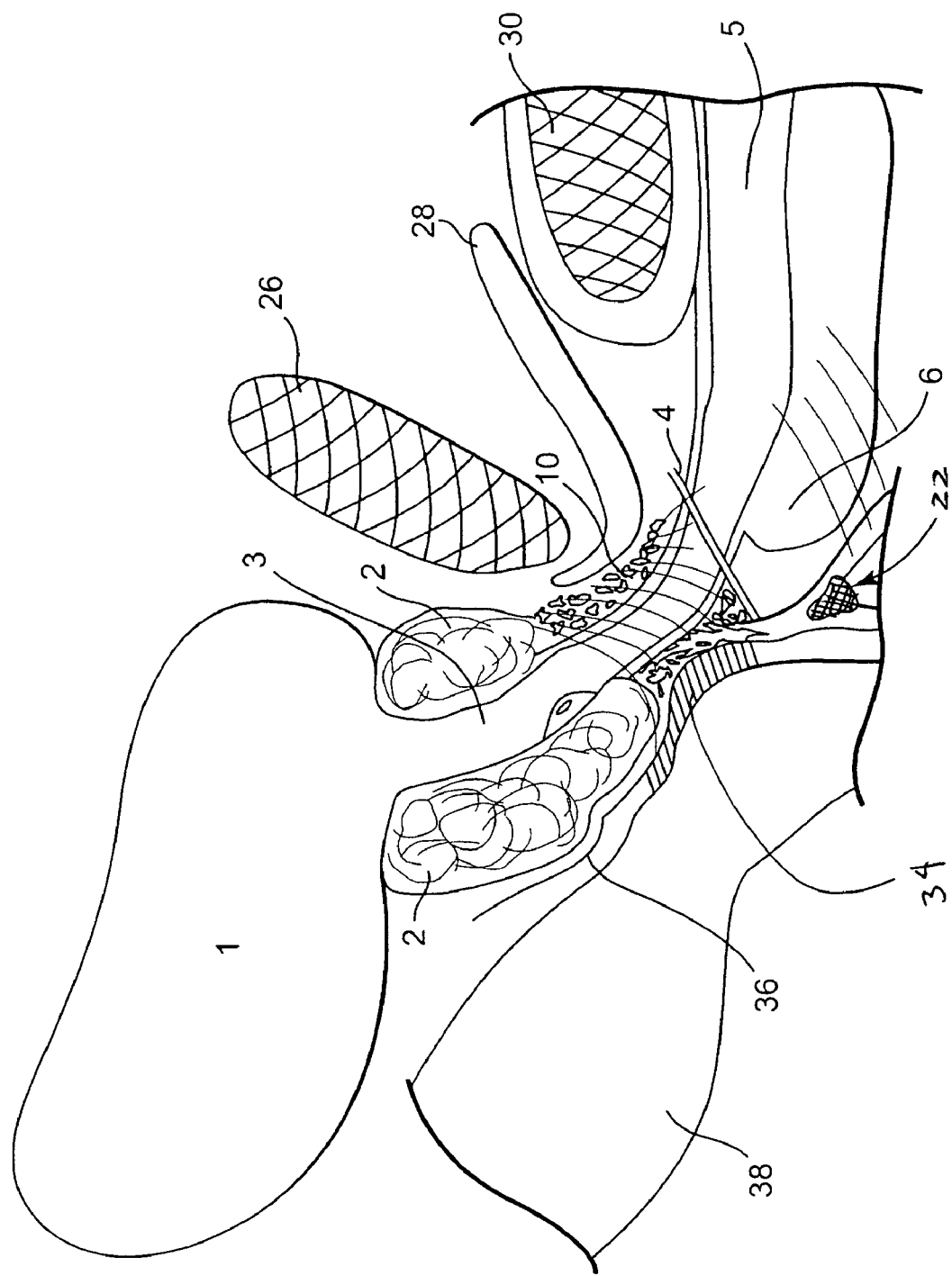
FIG. 2 illustrates general pelvic anatomy.

FIG. 2 shows features as in FIG. 1, and additional anatomical features. Rhabdosphincter 10 is a complex of muscles that extends from a position that includes the distal portion or "apex" of prostate 2, to and including the urethra positioned at perineal membrane 4, i.e., the "membranous urethra." FIG. 2 illustrates rhabdosphincter 10, bladder 1, pubic symphasis 26, dorsal vein 28, corpus cavernosum 30, rectum 38, corpus spongiosum 6, bulbospongiosus muscle 7, and prostate 2. Also illustrated are central tendon 22, rectourethralis muscle 34, and Denonvilliers' Fascia 36.

Referring to FIG. 2, rhabdosphincter 10 partially surrounds (circumferentially) urethra 3 starting at a position at the lower (distal) portion or "apex" of prostate 2 and continuing distally from prostate 2 to perineal membrane 4. In a person with healthy pelvic tissue, the manner by which rhabdosphincter 10 partially circumferentially surrounds urethra 3 may be generally considered to include a crescent-shaped or omega-shaped body of tissue that covers anterior and lateral portions of urethra 3. Moving distally from prostate 2 toward perineal membrane 4, the crescent shape of rhabdosphincter 10 gradually reduces to cover a smaller lateral area of urethra 3. With healthy and well-positioned rhabdosphincter and urethral tissue, rhabdosphincter 10 effects continence by contracting to cause coaptation of urethra 3 along the length of urethra 3 that is partially surrounded by rhabdosphincter 10.

FIG. 2 can illustrate healthy pelvic tissue in a continent male, but may also include tissue that has become weakened, sagged, or has experienced prolapse for any of a variety of reasons such as partial prostatectomy, other treatment of the prostate, age, or any other cause of a loss of muscle or tissue strength. Such an individual may also exhibit a condition of incontinence. Exemplary conditions of incontinence may be due to sagging of urethra 3 (e.g., at the posterior) in a manner that reduces or prevents the ability of rhabdosphincter 10 to cause complete or maintained coaptation of urethra 3.

Figure 3:
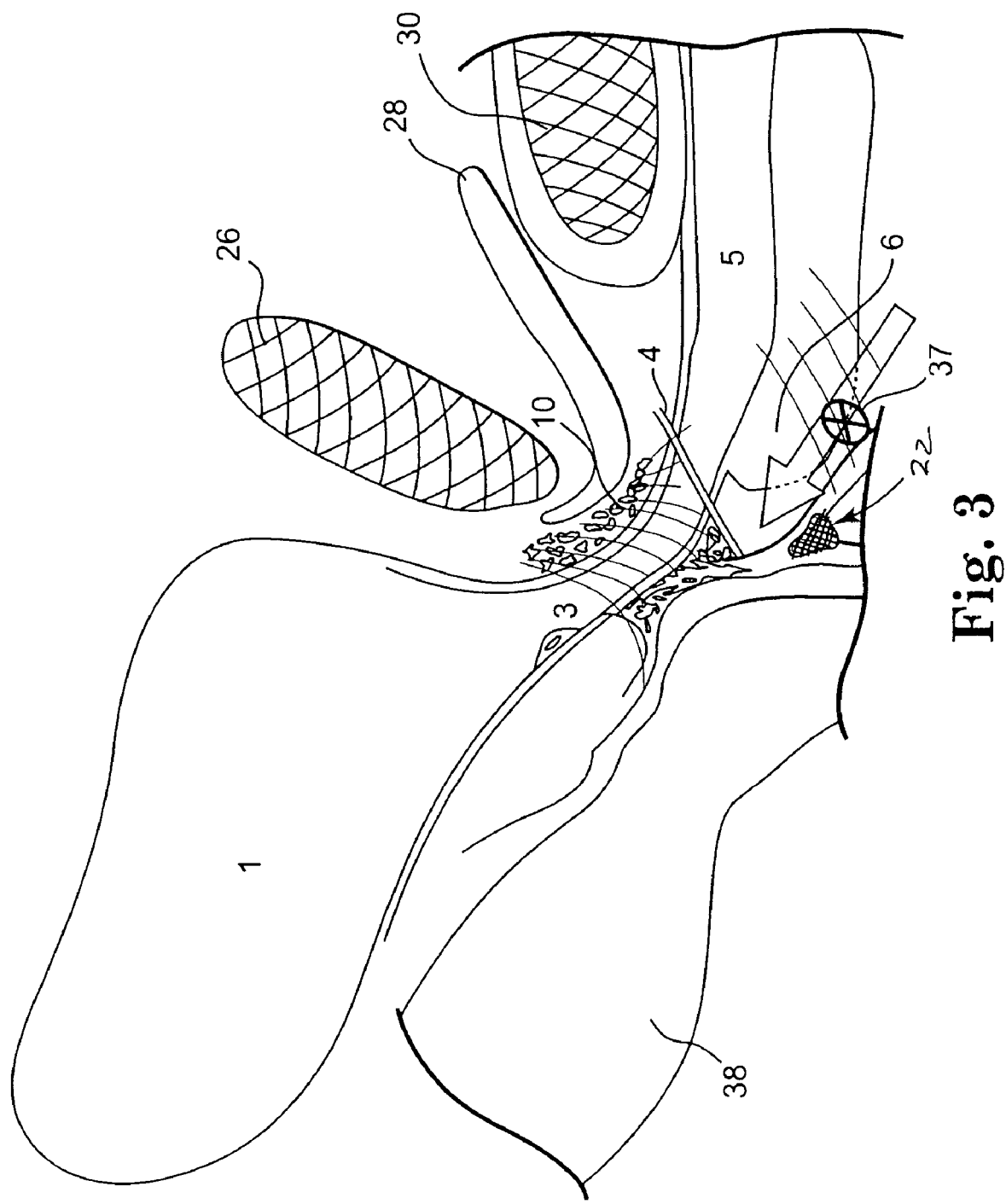
FIG. 3 illustrates general pelvic anatomy.

Incontinence may also be a result of complete removal of the prostate. FIG. 3 illustrates pelvic anatomy of a male patient having had a radical prostatectomy. In the illustrated anatomy, urethra 3 has been severed above and below the prostate (removed) and the urethra has been rejoined. A portion of the rhabdosphincter that was associated with the distal prostate is also removed, leaving a smaller rhabdosphincter 10 originally associated with the non-removed portion of urethra 3 and perineal membrane 4. Importantly, removal of the prostate may normally also damage tissue that supports the posterior of urethra 3. In specific, after radical prostatectomy a patient may exhibit damaged, disconnected, or removed tissue including one or more of rectourethralis muscle 34 and Denonvilliers' Fascia 36, tissues that would otherwise support urethra 3 at the posterior of urethra 3. Without support from either or both of rectourethralis muscle 34 or Denonvilliers' Fascia 36, urethra 3 (e.g., at the posterior) may become prolapsed and no longer be positioned relative to rhabdosphincter 10 in a manner that allows complete or maintained coaptation of urethra 3.

Figure 4:
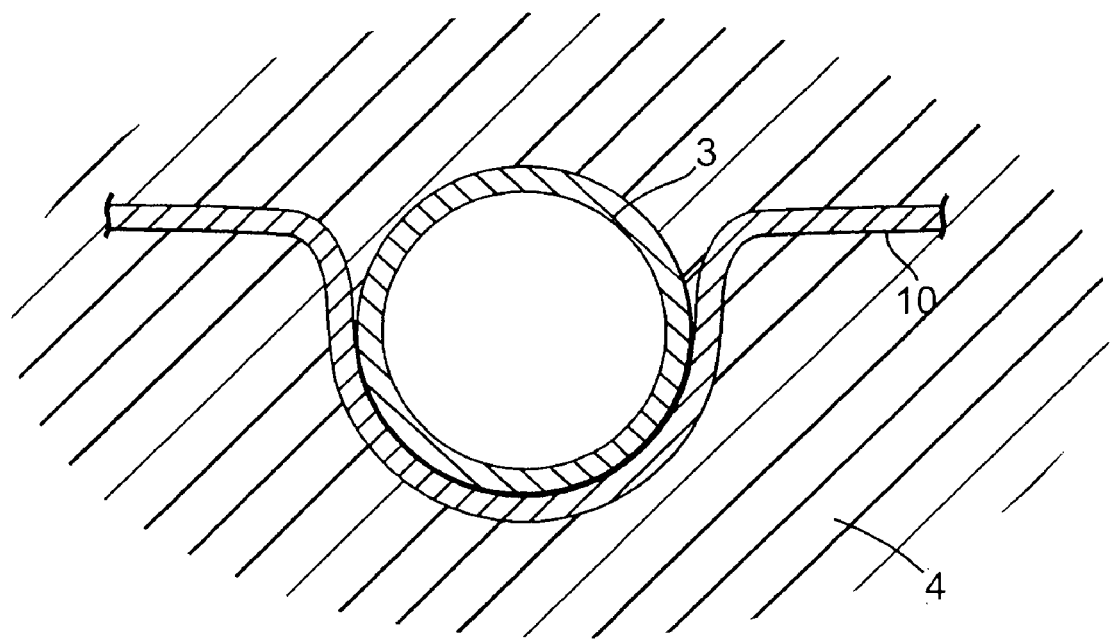
FIG. 4 illustrates anatomy including the rhabdosphincter and urethra.
Figure 5:
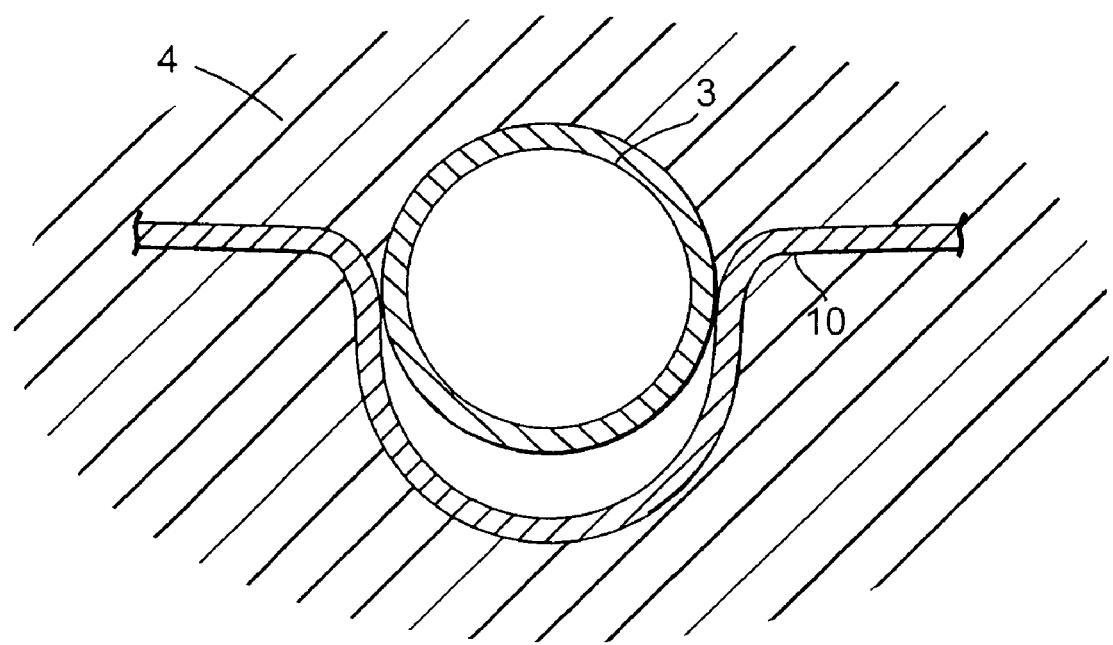
FIG. 5 illustrates anatomy including the rhabdosphincter and urethra.

FIG. 4 illustrates a healthy condition and proper spatial relation between rhabdosphincter 10 and urethra 3, e.g., near perineal membrane 4. FIG. 4 is a cross-sectional view of rhabdosphincter 10 relative to urethra 3 along the longitudinal axis of urethra 3. The perimeter of urethra 3 matches the shape of the curved region of rhabdosphincter 10. Upon contraction of rhabdosphincter 10, urethra 3 coapts to prevent flow of urine. FIG. 5 illustrates urethra 3 that is not in a healthy relationship with rhabdosphincter 10. Urethra 3 is shown to have sagged or prolapsed distally or posteriorly relative to rhabdosphincter 10 so that rhabdosphincter 10 no longer properly surrounds urethra 3 and is not able to effect complete coaptation of urethra 3.

Referring back to FIG. 1, and according to exemplary embodiments of inventive methods of treating incontinence, a urethral sling (20, shown in cross section) can be placed in a position to approximate and support pelvic tissue such as urethra 3, optionally and preferably without placing compressive forces on urethra 3, to effect improved continence. Preferably, sling 20 contacts corpus spongiosum 6 and is tensioned to cause approximation of corpus spongiosum 6 and urethra 3 in a proximal direction, toward bladder 1. Accordingly, embodiments of the invention generally relate to placement of a urethral sling at a location that supports and is tensioned to proximally re-position urethra 3. Sling 20 is tensioned to cause urethra 3—especially the posterior portion of urethra 3 above perineal membrane 4—to be moved from an abnormal (e.g., prolapsed or descended) position to a position of normal healthy urethral tissue capable of being fully coapted upon contraction of the rhabdosphincter.

According to these embodiments, a method of surgically installing a urethral sling can include providing a medial incision at the perineum of a male patient to expose bulbospongiosus muscle 7, optionally and preferably dissecting through bulbospongiosus muscle 7 to expose corpus spongiosum 6, and placing a central support portion of a urethral sling in contact with corpus spongiosum 6. Optionally the central support portion of the sling can be fixed to corpus spongiosum 6, such as by use of a medical attachment in the form of a suture, staple, adhesive, or the like. Sling 20 is tensioned to approximate pelvic tissue such as urethra 3, to improve continence, and tension can optionally and preferably maintained chronically.

Without further limiting the above description of the general invention, exemplary positioning of a urethral sling for tensioning to improve the position of urethra 3 relative to rhabdosphincter 10 can be below the urethral bulb in contact with the corpus spongiosum, as illustrated in FIGS. 1 and 3. Referring to FIG. 3, mark X, 37, in FIG. 3, indicates a useful position for contact between a urethral sling (not specifically shown) and corpus spongiosum 6. Arrow 40 indicates a useful direction of approximation of urethra 3 and corpus spongiosum 6 upon placing tension on end portions of an installed urethral sling. The direction of approximation shown by arrow 40 is tangential to and along the axis of urethra 3 at the bulbar urethra and perineal membrane 4. Tension that moves these tissues in the direction of arrow 40 will move urethra 3 in a proximal direction.

Placement of a central support portion of a sling at a location as illustrated in FIG. 1 or 3, and tension in the direction of arrow 40, allow the sling to approximate and support the posterior junction between the bulbar urethra 5 and the perineal membrane 4; e.g., the central support portion can be located and positioned to support the bulbar urethra 5.

Placement of the urethral sling and support of the described pelvic tissue as discussed herein and as exemplified by FIGS. 1 and 3, differ from certain past methods of treating male urinary incontinence, which can involve compressing the urethra to create a partial obstruction to the flow of urine. Such methods include installation of an artificial urinary sphincter at a location that is more distal along the urethra compared to the location of a urethral sling as shown in FIGS. 1 and 3, or retropubic installation of a urethral sling, also generally with placement of a urethral sling at a position more distal compared to the location shown in FIGS. 1 and 3. In the exemplary embodiment of the present invention illustrated at FIGS. 1 and 3, a central support portion of a sling can be located at a position along the urethra that is more proximal to the bladder in comparison to locations of an artificial urinary sphincter or a retropubic urethral sling. Those other methods locate a sling more distally along the bulbar urethra relative to the bladder and perineal membrane, with the intent of compressing the bulbar urethra to improve continence. A useful location of an installed sling according to the presently-described invention can be more directly below the membranous urethra.

Figure 6:
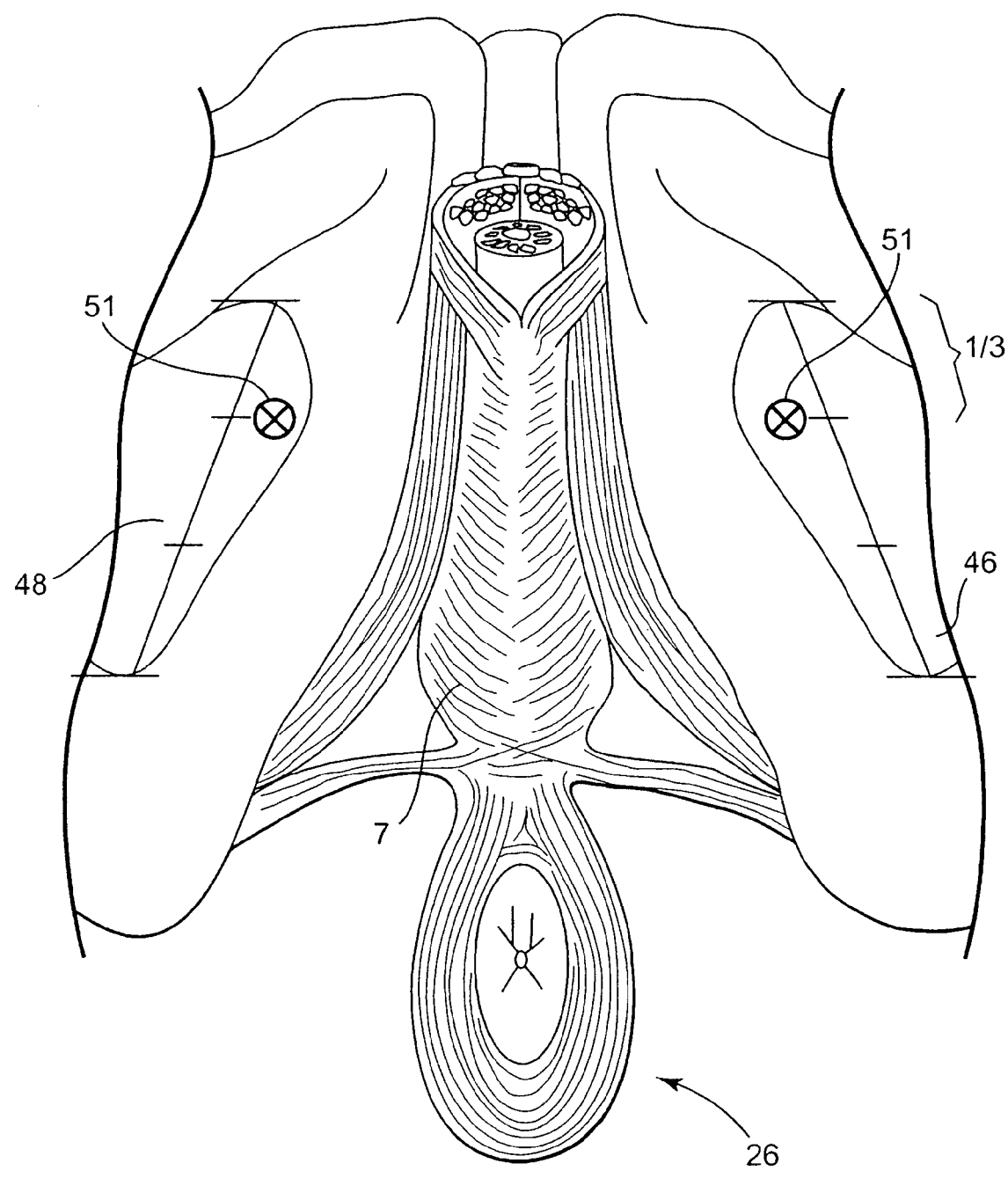
FIG. 6 illustrates general pelvic anatomy.
Figure 7:
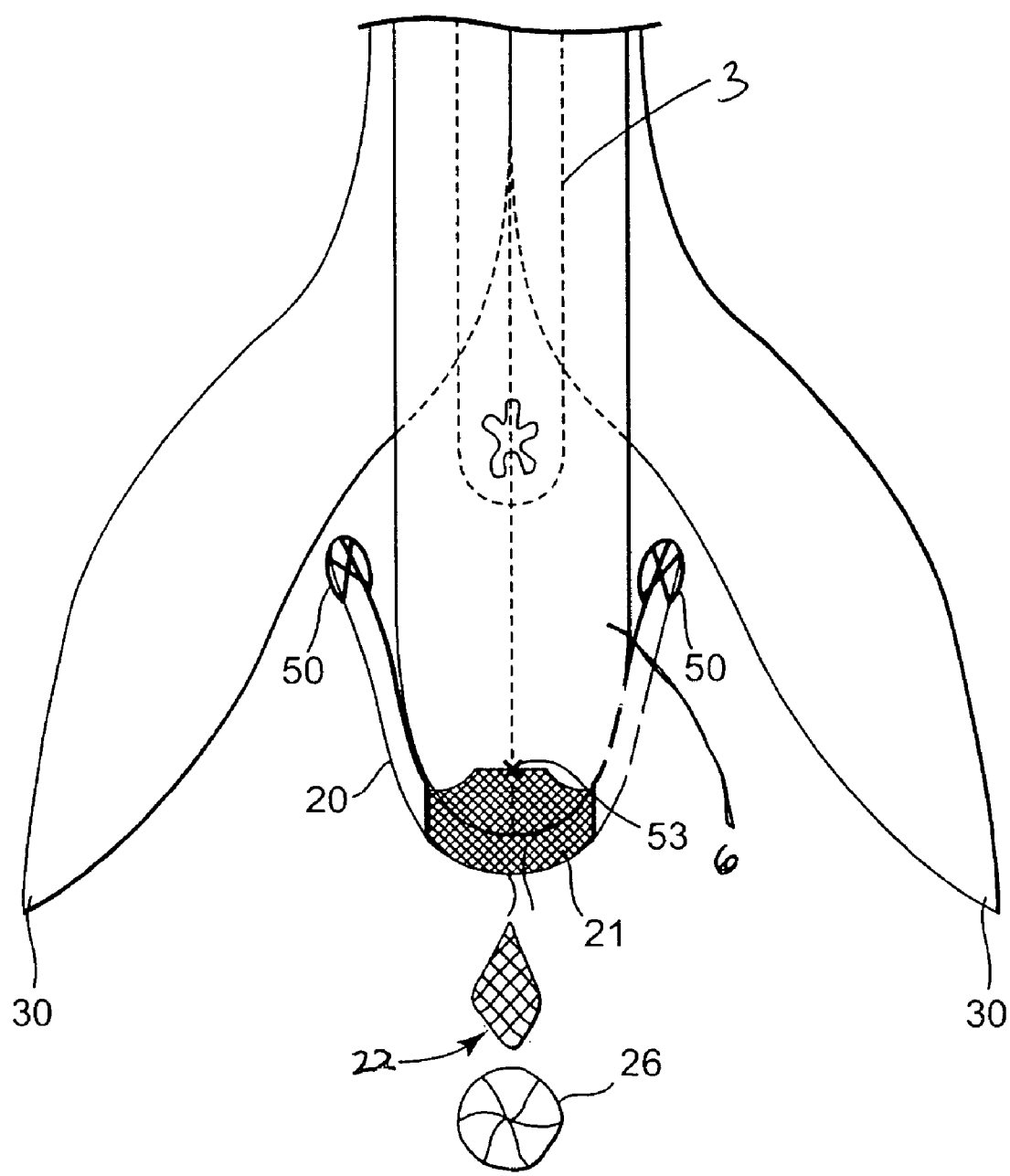
FIG. 7 illustrates general pelvic anatomy.

FIGS. 6 and 7 illustrate exemplary steps of installation of a urethral sling to treat incontinence according to the invention. FIG. 6 illustrates relevant tissue and bone structures, showing a perineal region of a patient lying in a dorsal lithotomy position. In FIG. 6, bulbospongiosus muscle 7 is shown intact, between left and right obturator foramen 46 and 48, respectively. Anus 26 lies below central tendon 22.

FIG. 6 also shows left and right tissue passages 51 at the left and right obturator. Preferred locations for passages 51 through the left and right obturator foramen are as high as possible on the obturator foramen, such as at the upper ⅓ of the medial part of the obturator foramen. A high passage allows for the application of maximum lift on the sling, urethra, or corpus spongiosum, etc., upon tensioning the sling. Maximum lift provides maximum tangential force on the urethra to allow optimal or maximal movement of the urethra proximally.

At FIG. 7, bulbospongiosus muscle 7 (not shown) has been dissected along a medial path and placed or folded bi-laterally to the left and right to expose corpus spongiosum 6. Urethra 3, indicated by a dashed line, lies below corpus spongiosum 6. marks X identify left and right tissue path entries 50 between corpus spongiosum 6 medially and each of two lobes 30 of corpus cavernosum laterally. Central support portion 21 of a urethral sling 20 is illustrated to contact corpus spongiosus 6 below urethra 3 (dashed lines) with end portions extending laterally in left and right directions to tissue path entries 50. Central support portion 21 is illustrated to have a width greater than the width of end portions of sling 20. Optional suture 53 has been placed on the distal (anterior) portion of the central support portion to ensure that a distal portion or lobe of central support portion 21 does not fold or become misshapen upon application of tension to sling 20. Central tendon 22 is shown below bulbospongiosus muscle 7, as is anus 26.

According to a preferred dissection, tissue that surrounds or contacts corpus spongiosum 7 to hold corpus spongiosum 7 in place distally may be dissected to allow corpus spongiosum 7 (and associated urethra 3) to be moved proximally upon tensioning an installed sling. In specific, bulbospongiosus muscle 7 normally attaches medially onto corpus spongiosum 6, and laterally toward the inferior pubic rami and corpora cavernosa 30. According to a preferred procedure, dissection can be performed to reach but not go past central tendon 22, but also not to reach or damage anus 26. Dissection up to but not through central tendon 22 disconnects corpus spongiosus 6 from bulbospongiosus muscle 7, which allows freedom of movement of corpus spongiosus 6 and the ability to move corpus spongiosus 6 proximally upon tensioning of a sling 20 installed below corpus spongiosus 6.

Certain features of the invention have resulted from careful examination, including ultrasound observation, of pelvic anatomy of men who suffer from urinary incontinence. Based on these examinations the observation was made that incontinence may be associated with mis-placement of the urethra due to conditions of prolapse, perineal descent, muscle weakness or failure, or other conditions that cause misplacement of pelvic tissue such as the urethra, rhabdosphincter, or both. The urethra or rhabdosphincter may mis-positioned, impaired, or damaged, for example, due to any one or more of: radical prostatectomy, other urological surgery, increased mobility of the perineal floor, male prolapse, perineal descent, etc. Due to any one or more of these conditions, a rhabdosphincter can exhibit reduction in efficiency, or a urethra may exhibit mis-placement relative to an anatomically normal position in association with the rhabdosphincter, resulting in symptoms of incontinence.

An example of an abnormal physiologic condition of a urethra relative to a rhabdosphincter is illustrated at FIG. 5, which is a cross-sectional view (at perineal membrane 4) of rhabdosphincter 10 relative to urethra 3 along the longitudinal axis of urethra 3. FIG. 5 illustrates a condition of urethra 3 as being not properly associated with rhabdosphincter 10. Specifically, urethra 3 has sagged or prolapsed posteriorly causing the perimeter of urethra 3 to not match the shape and position of rhabdosphincter 10. Upon contraction of rhabdosphincter 10, urethra 3 will not properly coapt to prevent flow of urine, or will be unable to prevent loss of urine under an abdominal stress event like a cough, sneeze, or a sudden contraction of the muscles of the torso when lifting a heavy object.

Thus, according to embodiments of the invention, a urethral sling can be used to correct for a loss of efficiency of the rhabdosphincter or misplacement of the urethra relative to the rhabdosphincter. A urethral sling can be implanted, positioned, and tensioned to re-position and support pelvic tissue such as the urethra or to re-position a misplaced urethra in a proximal direction, to improve positioning of the urethra relative to the rhabdosphincter and to thereby provide for improved and desirably complete urethral coaptation and continence. The sling may be placed in contact with the corpus spongiosum after dissecting through the bulbospongiosus muscle, and then tensioned to adjust and correct the position of the urethra for coaptation by the rhabdosphincter. The sling may optionally be fastened to the corpus spongiosum either before or after tensioning and adjustment of the sling and any desired approximation of pelvic tissue such as the corpus spongiosum or urethra. An exemplary placement of a suture or other surgical attachment can be at an anterior edge or extension of the central support portion.

A misplaced urethra relative to the rhabdosphincter can result from extended or dis-located pelvic tissue, such as by tissue extension in the direction toward an anterior or distal location, toward the meatus. Embodiments of the invention relate to re-positioning such misplaced or damaged tissue to improve continence, by implantation of a support or sling. With reference to FIGS. 4 and 5, a misplaced or damaged rhabdosphincter 10 or urethra 3 as in FIG. 5, resulting in a loss of continence, may be re-positioned to a normal anatomical position as illustrated in FIG. 4, allowing for coaptation of urethra 3 and improved or complete continence.

More specifically with respect to this particular embodiment of the invention, but still by way of example, a urethral sling may be sutured to the corpus spongiosum at a location that will allow the sling to be tensioned to support pelvic tissue such as the urethra, rhabdosphincter, or both, and to re-position the rhabdosphincter, urethra, or both, to anatomically more correct positions. The particular location of placement of the sling may depend on the exact condition of the patient and the extent of misplacement of pelvic tissue, e.g., perineal descent, or mis-placement of the urethra or rhabdosphincter. As an example, a sling may be placed against the corpus spongiosum to allow for approximation of the corpus spongiosum by a distance of about 0.5 to 4 centimeters, e.g., 0.5 to 1.5 centimeters, or 1 cm, in a posterior direction. To achieve this amount of approximation the sling may be placed at a location that is about 0.5 to 4 centimeter (e.g., 0.5 to 1.5 cm) distal from (anterior to) the expected final sling location. The sling and corpus spongiosum may then be approximated to the posterior by the desired distance from 0.5 to 4 centimeters e.g., 0.5 to 1.5 centimeters.

In alternate embodiments, the sling may be placed as desired at the corpus spongiosum, the sling may be tensioned and tissue such as the corpus spongiosum, urethra, perineal body, etc., may be approximated. Optionally, the sling may be fastened to the corpus spongiosum, e.g., using a suture, stapler, or other medical fastening device or mechanism.

In the exemplary embodiment, approximation of the corpus spongiosum can cause movement or relative movement of or between the urethra and the rhabdosphincter to allow the rhabdosphincter to better coapt the urethra and achieve improved or complete continence. Again not wishing to be bound by theory, approximating the corpus spongiosum may have the therapeutic effect of lifting and rotating (in a clockwise direction when viewed in the cross-section of FIGS. 1, 2, and 3) tissue of the urethra, rhabdosphincter, or both, into a more physiologically normal position. As shown in FIG. 3, the urethra can be moved in a direction parallel to the lengthwise direction of the urethra. Upon tissue ingrowth into the sling, the rhabdosphincter will have a more rigid backboard by which to operate against when collapsing the urethra. Improved positioning of the rhabdosphincter can be especially useful for men who have had the dorsal rhabdosphincter ruptured due to radical prostatectomy, and the muscle can no longer work against itself to collapse the urethra but rather needs to work against another rigid structure to be efficient.

Optionally, a cystoscope may be used before, during, or following an installation procedure. Pre-operatively, a cystoscope may be useful to identify whether a patient exhibits residual sphincter function. Patients having at least some degree of residual sphincter function have been found to be better candidates for a procedure of the invention compared to patients that exhibit no residual sphincter function. Thus, a cystoscope may be used to identify whether a patient is capable of voluntary coaptation of the urethral sphincter, and if so the patient may be a good candidate for the procedure described herein. Intraoperatively, a flexible cystoscope may also be used, if desired, to monitor the urethra upon tensioning of a sling during installation, especially for surgeons learning the procedure.

A urethral sling for use in the described transobturator methods can generally be of the type useful as an implanted surgical device for treating male or female urinary incontinence, either presently known developed in the future. Exemplary urethral slings are discussed in U.S. Pat. No. 6,911,003 and in Published U.S. Pat. Appl. No. US 2003/0171644A1. Useful slings can be described as having two end portions extending in generally opposite directions from a central support portion.

A sling for use according to the invention can be any urethral sling, known or developed in the future. A transobturator method on the male anatomy can involve passage of a sling through substantial muscle mass, and once installed the sling may be subjected to relatively large forces from the male muscle mass or from the strength of the male anatomy. Also, preferred methods of the invention place the sling at the corpus spongiosum, which is a spongy and deformable tissue. A sling used for the male transobturator installation as described herein may include certain features that will allow for usefulness, ease of use, improved contact between the sling and the corpus spongiosum, and longevity of the treatment, considering the average male anatomy (in comparison with average female anatomy). For instance, a preferred sling for use with a male transobturator method described herein may include features that improve short-term fixation of the sling, long-term fixation of the sling, reinforced end portions, and a widened central support portion for contacting the corpus spongiosum.

A preferred sling for placement against a corpus spongiosum may also include a widened central support, for increased contact and frictional engagement with the corpus spongiosum. According to embodiments of the invention, the sling can be tensioned to approximate corpus spongiosum proximally. A widened central support portion can provide improved mechanical and frictional engagement between the central support portion and the corpus spongiosum. A widened central support portion provides a larger area of contact between the sling and corpus spongiosum, and can have a reduced tendency to fold or deform upon tensioning of the sling. A suture can be used to attach the central support portion to the corpus spongiosum to further improve the area of contact and prevent folding, such as at a location on the anterior side of the central support portion. A suture may also be useful to prevent movement of the sling relative to the corpus spongiosum during or after installation or tensioning.

Exemplary pelvic urethral sling implants that can include a widened central support portion, such as described in Assignee's copending U.S. patent application Ser. No. 11/346,750, entitled "TRANSOBTURATOR SURGICAL ARTICLES AND METHODS, filed on even date herewith, the entirety of which is incorporated herein by reference.

A widened central support portion has a width that is greater than a width of the end portions, e.g., the width of the end portion at a location that is adjacent to the load-transfer portion. A central support portion that has a width that is greater than a width of the end portions can improve contact between the implant and tissue to be supported by the implant, e.g., corpus spongiosum. An increased width of a central support portion may take the form of one or two lateral extensions or "lobes" that extend laterally in at least one direction (an anterior direction) for contacting tissue being supported. An anterior extension supports tissue that is relatively anterior to a patient's anatomy compared to an otherwise similar central support portion that exhibits a smaller width. Alternately, a central support portion may include two lateral extensions in each of an anterior lateral direction and a posterior lateral direction, to contact tissue both anterior and posterior to a central support portion of a relatively more narrow width.

An increased width, e.g., in an anterior direction, can provide for increased contact and frictional engagement between a central support portion and pelvic tissue such as a urethra or tissue that supports the urethra, e.g., bulbous spongiosum. A widened central support portion provides a larger area of contact between the sling and a tissue and can have a reduced tendency to fold or deform upon tensioning of the sling. Increased contact area between a central support portion and pelvic tissue can further allow for improved ability to relocate or approximate tissue if desired during implantation of the sling and treatment and support of pelvic tissue by use of the sling.

Adjacent to a central support portion, and connecting the central support portion to one or preferably to both end portions, can be one or two load-transfer portions. The load-transfer portion exhibits a width that is greater than a width of an end portion, such as the width of the end portion at the location at which the end portion connects to the load-transfer portion. The load-transfer portion also includes a width that is less than the width of the central support portion. Functionally, the load-transfer portion allows a load placed across the central support portion, between the end portions, to be distributed across a width of the central support portion that is greater than widths of the end portions.

The central support portion is of sufficient length to support and optionally partially surround a pelvic tissue, e.g., to treat incontinence, such as to support the urethra or urethra-supporting tissue (optionally in combination with some or a portion of the length of load-transfer portions). A width of a central support portion is greater than a width of end portions and is sufficiently wide to increase contact area and frictional forces between a central support portion and a tissue in contact with the central support portion. Exemplary lengths of a central support portion can be in the range from 0.5 to 2 centimeters, such as from 1.2 to 1.8 centimeters. Exemplary widths of a central support portion can be in the range from 1.5 to 4 centimeters, such as from 2 to 4 centimeters. A combined length of two end portions, a central support portion, and one or more load-transfer portion or portions, can be approximately 16 inches (about 41 centimeters), e.g., within the range from 35 cm to 50 cm. Alternate lengths can also be used.

Figure 8:
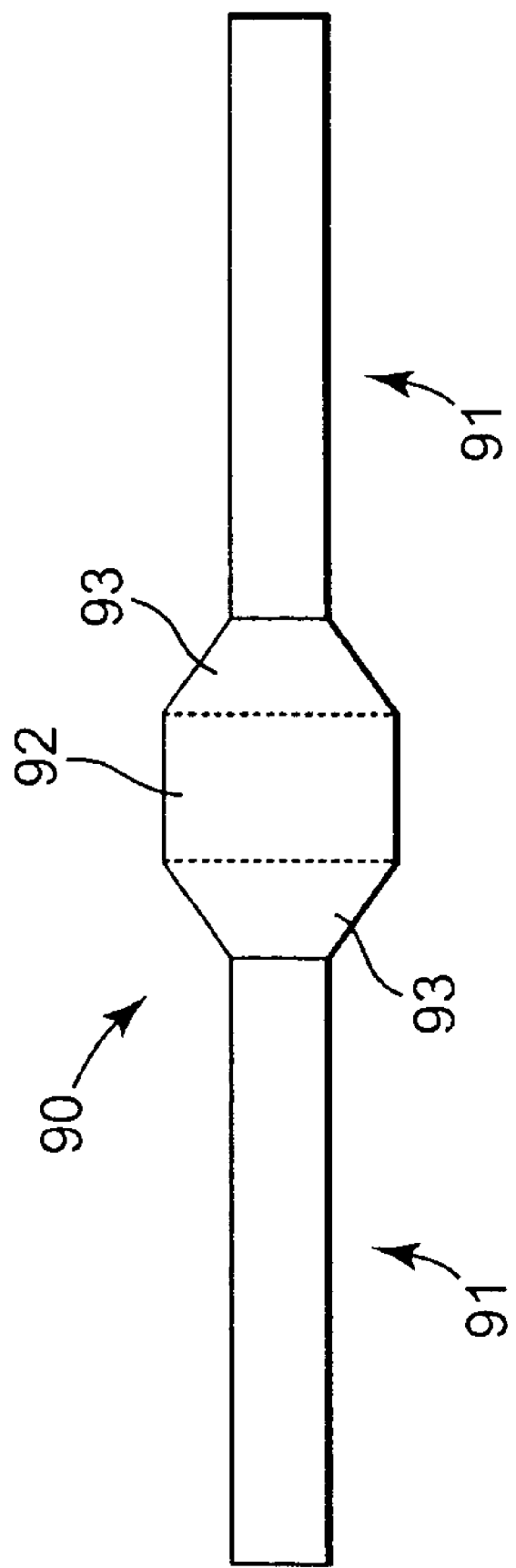
FIG. 8 illustrates an exemplary urethral sling for use according to the invention.

FIG. 8 shows a sling 90 with a shape other than a purely rectangular shape. This embodiment of sling 90 includes two end portions 91, a mid portion (central support portion) 92 that is wider than the remaining (e.g., end) portions of the sling 90, and load-transfer portions 93 connecting each of end portions 91 to central support portion 92. An anterior extension of central support portion 92 and load-transfer portions 93 extends laterally (in the width direction), in an anterior direction. A posterior extension of central support portion 92 and load-transfer portions 93 extends laterally and posteriorly.

A urethral sling may be integral, monolithic, or a composite of different components or segments of different synthetic or non-synthetic (e.g., "biologic") components. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals, and plastics and any combination of such materials.

Examples of synthetic sling materials include polypropylene, cellulose, polyvinyl, silicone, polytetrafluoroethylene, polygalactin, Silastic, carbon-fiber, polyethylene, nylon, polyester (e.g. dacron) PLLA and PGA. The sling material may be resorbable, absorbable, or non-absorbable. Optionally, some portions may be absorbable and other portions may be non-absorbable. Commercial examples of synthetic materials useful in a urethral sling include Marlex™ (polypropylene) available from Bard of Covington, RI, Prolene™ (polypropylene) and Mersilene (polyethylene terephthalate) Hernia Mesh available from Ethicon, of New Jersey, Gore-Tex™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in U.S. Pat. Application No. 2002/0072694.

A sling can include end portions that include side edges ("edges"), and the edges can optionally include edge extensions. Edge extensions refer to solid extensions of a non-uniform edge, interrupted by non-solid open spaces. Edge extensions can result from molding, cutting, or other formation of a solid or a porous our "open pore" end portion material. Exemplary edge extensions can be due to the open pore nature of a material used to prepare an end portion of a sling, and the process of cutting the material along a line that includes the pores to produce an edge.

For use according to the present description, edge extensions of an end portion of a sling can optionally be reinforced to cause the end portion to resist movement within tissue to increase short-term fixation properties of the sling. Reinforced edge extensions provide increased frictional resistance of an end portion from movement within the tissue, which provides desired short-term fixation properties of end portions within tissue during and immediately after installation, i.e., the ability of the end portions to stick and hold into flesh when installed without moving. Also preferably the end portions may be tensioned with without substantial stretching.

According a first type of reinforcement, edge extensions can be reinforced by reinforcing open pore material adjacent to the edge (e.g., without treating the edge itself) in a way that limits movement of edge extensions and produces a stiffened edge extension. Other reinforcement can be in the form of a stiffening or reinforcing coating applied directly to edge extensions to limit the movement of the edge extensions. Reinforcement may also include combinations of treatments or structural features of edges or of areas of porous material adjacent to edges. Thus, a reinforcement may include or contact an edge (i.e., an end of an edge extension), may be adjacent to an edge but not include the edge (end of edge extension) itself, or may contact some portions along an edge of an end portion and not other portions along the same edge, while also including or contacting areas adjacent to the edge. With any of these reinforcements, the force required to pull a reinforced elongate strip through tissue can be increased.

Figure 9:
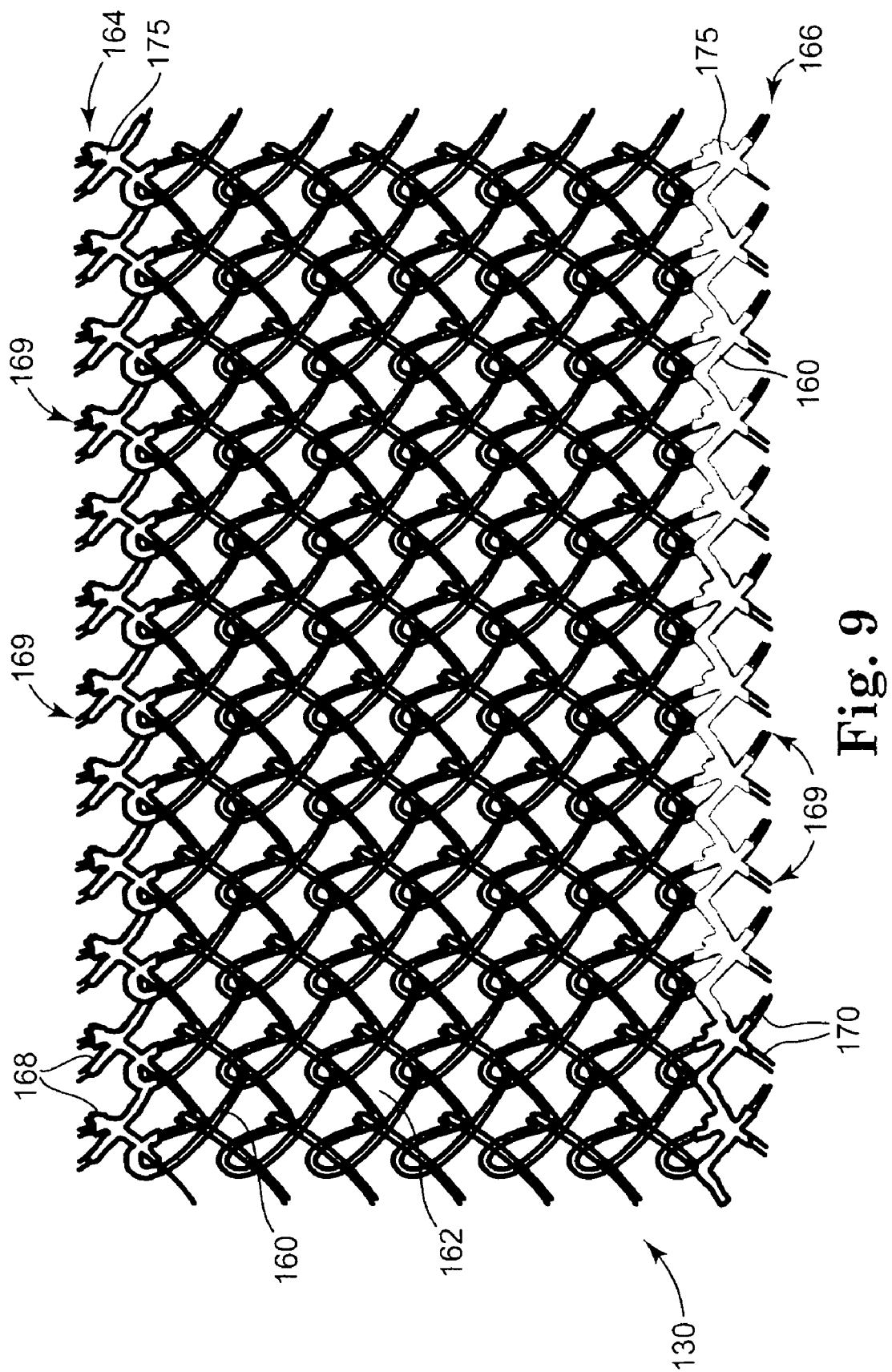
FIG. 9 illustrates a detailed view of an embodiment of an end portion of a urethral sling.

Exemplary reinforcement of an open pore mesh 130 is shown at FIG. 9. FIG. 9 illustrates open pore mesh 130 with edge treatment of edge extensions (severed strands) 168 and 170 in accordance with one aspect of the present invention. In FIG. 9, edge extensions 168 and 170 are reinforced by any one or more of a coating, heat treatment, or other mechanical or chemical treatment that stiffens edge extensions 168 and 170 at locations depicted by edge bands 174 and 176 (shaded edges). Strand ends 169 are shown not to be heat treated.

One exemplary urethral sling can be a strip or length of material of uniform width and thickness composed of interwoven fibers that can have spaced knots with or without heat set edges, such as the sling available under the MONARC™ trade name from American Medical Systems, Inc., of Minnetonka, Minn. A urethral sling may have stitching such as that of the MONARC™ sling, and may or may not include heat set edges or other reinforcement of edge extensions to increase strength of the sling or resistance to movement of the sling when the sling is in contact with tissue.

A central support portion is located between two opposing elongate end portions. The central support portion may be integral with the sling end portions as the same material, having the same width and thickness, or may be of another material having different width and thickness dimensions. The central support portion is attachable to or integral with the sling end portions and can be composed of a porous or non-porous plastic materials, a biologic material, or the like, such as a thermoplastic (e.g., polypropylene).

A synthetic sling or sling material may be prepared by any useful method, such as knitted, woven, sprayed, cut, punched from a blank, etc. Some slings may be sufficiently robust to be inserted without a protective sleeve. In other embodiments, some synthetic slings may have an associated protective sleeve to assist with the implantation. A useful mesh material may be prepared from one or more woven, knitted, or interlinked filaments or fibers that form multiple fiber junctions throughout the mesh. The fiber junctions may be formed via weaving, knitting, braiding, bonding, ultrasonic welding or other junction forming techniques, including combinations thereof. The size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As an example, not intended to be limiting, a useful mesh useful to construct a urethral sling may be woven polypropylene monofilament, knitted with a warp tricot. The stitch count may be 27.5 courses/inch (+ or −2 courses) and 13 wales/inch (+ or −2 wales). The thickness of this example is 0.024 inches. This embodiment of sling is preferably associated with a protective sleeve. Non-mesh sling configurations are also included within the scope of the invention.

Exemplary sling materials or end portions of a urethral sling can be inelastic. A mesh or end portion of a urethral sling may be tested to determine whether it is elastic or inelastic using a series IX Automated Materials Testing System (an Instron), available from Instron Corporation. A 1 cm wide sample of the mesh may be placed in the Instron with a crosshead speed set at 5 in/min and a gauge length of 1 inch. An elastic mesh exhibits at least a 7% elongation under a ½ pound load. An inelastic mesh exhibits less than a 7% elongation under a ½ pound load.

In one exemplary embodiment, a central support portion of a urethral sling can be substantially free of any silicone coatings. In yet another embodiment, a central support portion may comprise a non-synthetic material constructed according to the description of U.S. Provisional Patent Application No. 60/405,139, filed Aug. 22, 2002. Other suitable synthetic slings are described in U.S. Pat. No. 6,953,428.

A urethral sling for use according to this description may have one or more substances associated therewith through a process such as coating or they may be incorporated into the raw material of the sling. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, and resist infection or other effects.

While a sling for use in treating male incontinence according to the invention may typically be elongate and rectangular, other variations are also contemplated. The size of a sling can take into account the imprecision associated with the range of human anatomy sizes. In one embodiment, the sheath length of the assembly of the present invention is approximately within the range of 10 cm to 50 cm, sheath width is approximately within the range of 1.0 cm to 2 cm (e.g., from 1.1 cm to 1.5 cm wide), and sheath material thickness is approximately within the range of 0.127 mm to 0.203 mm, respectively. An associated sling has a length, width and thickness approximately within the range of 7 cm to 50 cm; 1.0 cm to 2 cm; and 0.508 mm to 0.711 mm, respectively.

Figure 10:
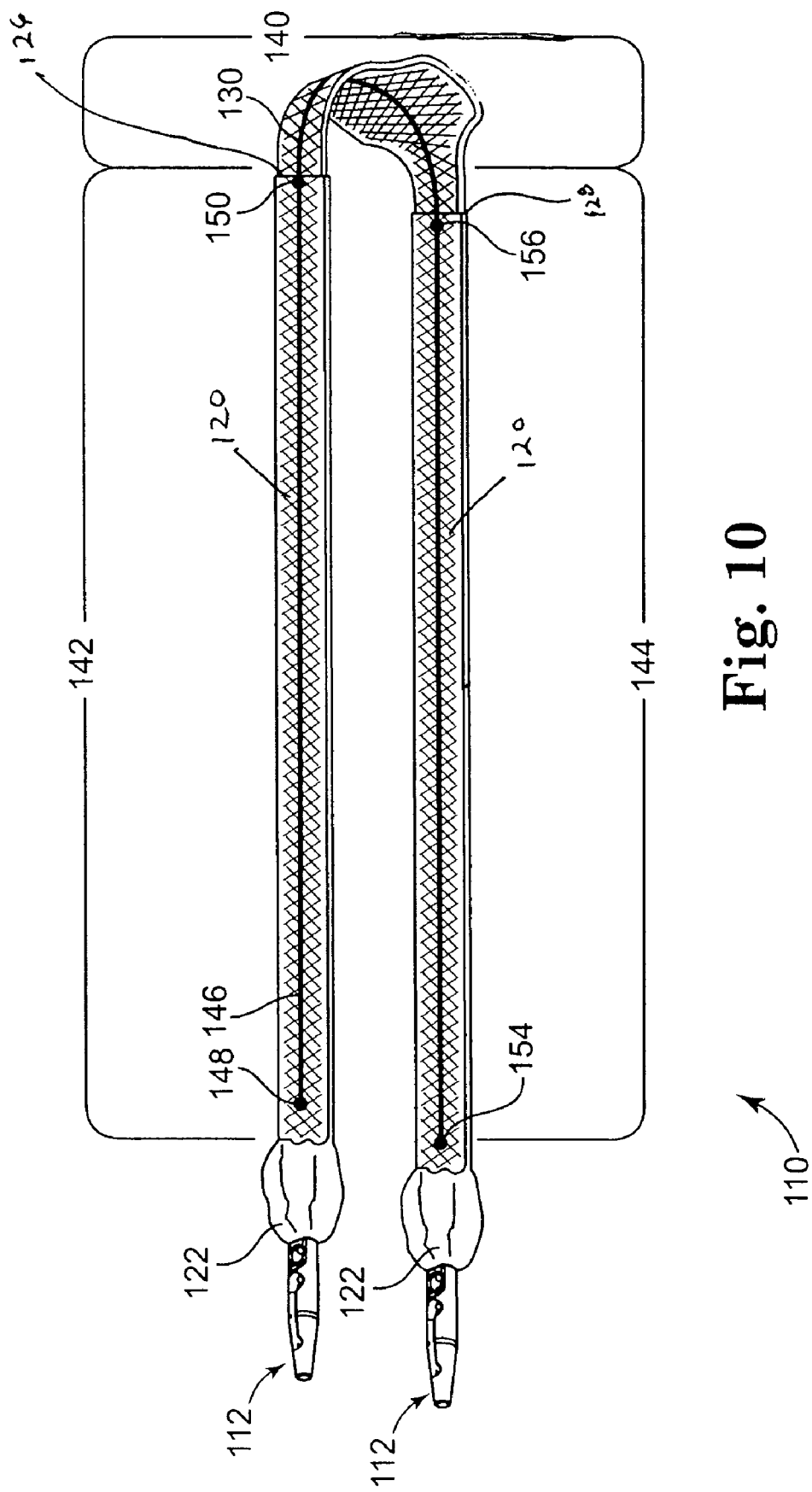
FIG. 10 illustrates an embodiment of a urethral sling.

Referring to FIG. 10, an exemplary embodiment of a urethral sling assembly is depicted. Sling assembly 110 includes sling end connectors 112, which engage with free ends of right hand and left hand sling implantation tools (not shown). End connectors (or "dilators") 112 can be shaped to dilate right and left passages through body tissue formed by curved needles of right and left hand implantation tools in a transobturator procedure. While not specifically illustrated, a sling as illustrated by FIG. 10 may include edge extension reinforcement as described above (e.g., a reinforcing coating, reinforcing weave, reinforcing strand, heat treatment, etc.).

Sling assembly 110 comprises urethral sling 120 enclosed within protective sheaths 122 extending from sling end connectors 112 and 114, respectively, to free and open sheath ends 126 and 128, respectively. Preferably, protective sheaths 122 are constructed of a flexible thin transparent plastic film that enables visual examination of urethral sling 120 and is sufficiently lubricious to pass easily through tissue passageways of a patient formed using sling implantation tools. Sheaths 122 can include sheath indicia or tear scores, perforations, or holes for assisting a surgeon in orienting urethral sling 110 relative to a urethra. Sling 120 can be left in place chronically following implantation.

Figure 11A:
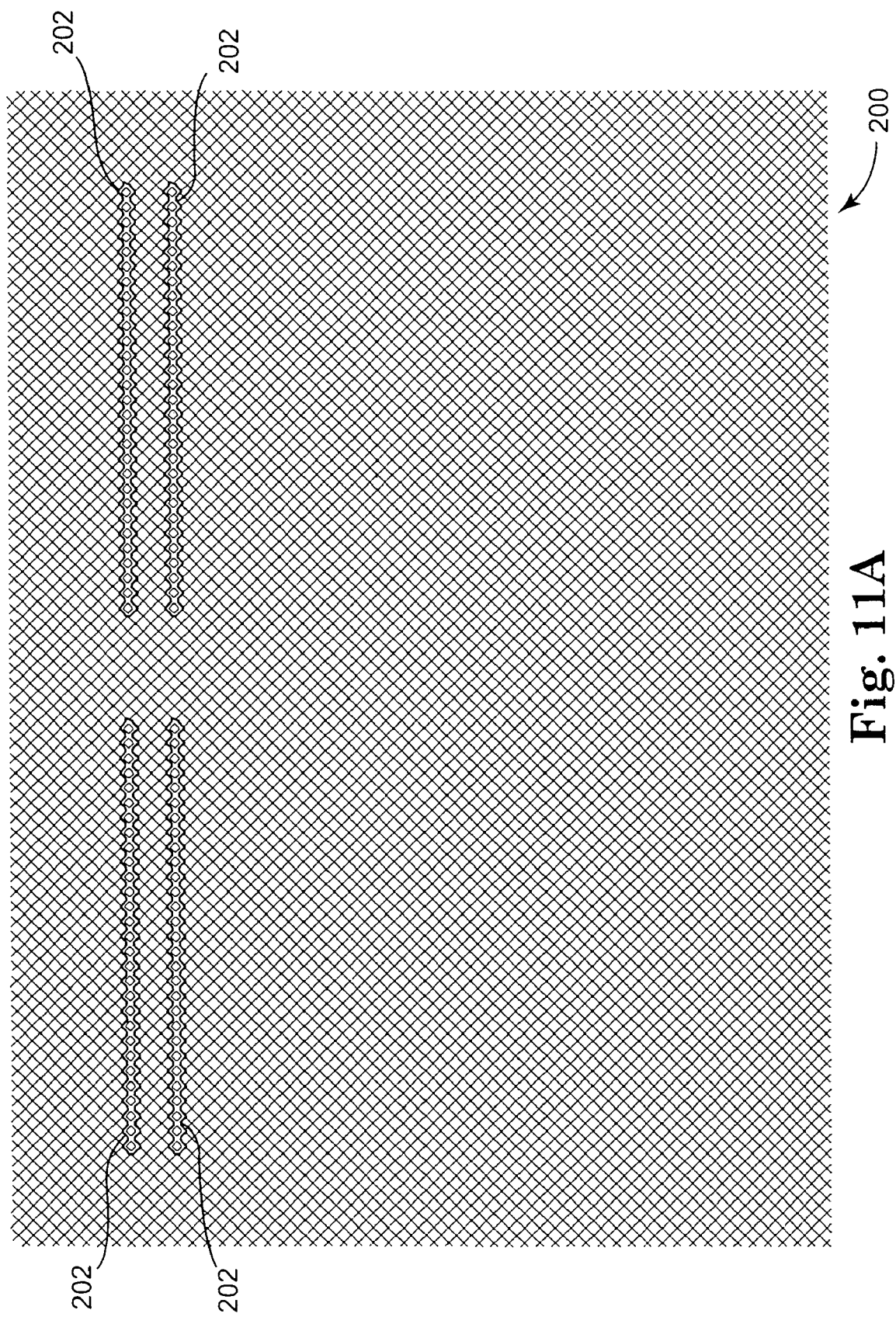
FIGS. 11A, 11B, and 11C, illustrate a porous material and an exemplary urethral sling prepared from the porous material.
Figure 11B:
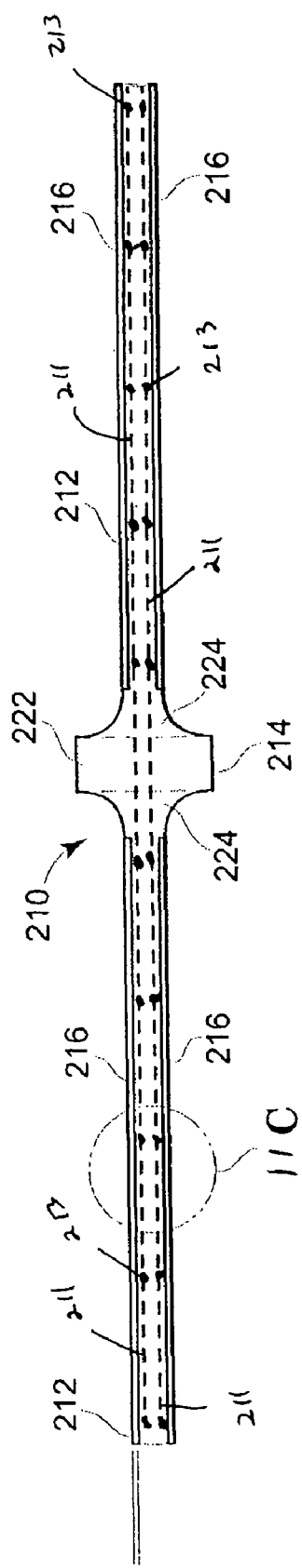
Figure 11C:
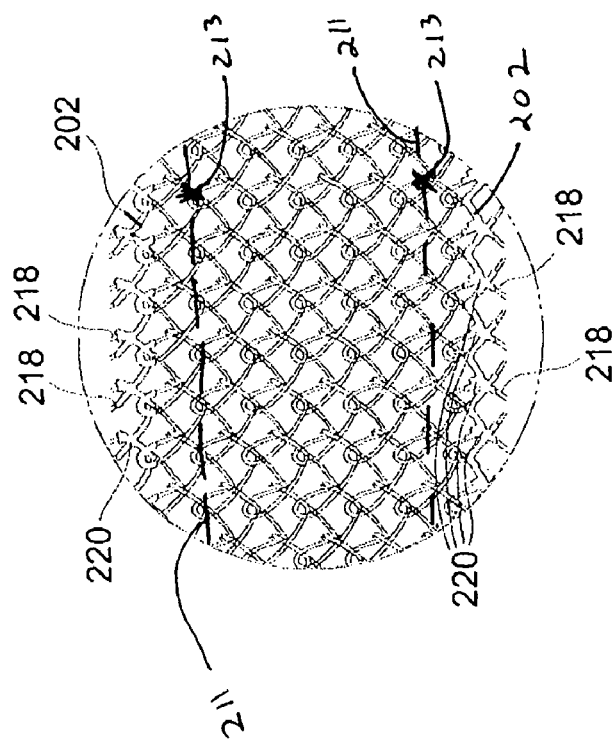

A specific example of a useful method for preparing an implant having reinforced edge extensions based on heat-treatment, is illustrated at FIGS. 11A, 11B, and 11C. FIG. 11A shows a sheet of open pore material 200, which is illustrated as a woven mesh but which may be any open pore material. Mesh sheet 200 is sized substantially larger than the total dimensions of a mesh implant that will be formed from sheet 200.

FIG. 11A illustrates treated (e.g., heat-treated, coated, etc.) open pore material 202. Treated material areas 202 can be in the form of lengths of heat-treated open pore material (e.g., mesh) extending along a desired path of open pore material. As an example, heat-treated open pore material 202 may uniformly contact a longitudinal area that includes a series of adjacent pores along a length of mesh 200. Alternately or in addition, heat-treated material 202 may uniformly contact a longitudinal area that includes a series of adjacent junctions of mesh strands (e.g., knots) or other junctions or intersections of mesh 200. Contacting either a series of adjacent pores or junctions of a porous material can result in a uniform pattern of heat-treated material, e.g., a uniform length-wise area of heat-treated junctions, a uniform length-wise of heat-treated pores, or an area that includes pores and junctions.

In one specific embodiment a heat-treated material 202 includes heat-treated junctions (e.g., knots or weaves) of a mesh material. With a location of heat treatment that includes a heat-treated junction of a mesh, cutting the mesh can be performed along a line that includes open pores that are immediately adjacent to and substantially parallel to the area that includes the series of heat-treated junctions. Upon such cutting step, edge extensions of non-heat-treated severed mesh strands result adjacent to elongate areas of heat-treated mesh junctions.

FIG. 11B illustrates an embodiment of a urethral sling cut from mesh 200 after formation of heat-treated material 202. Urethral sling 210 includes two extension portions 212 extending from central support portion 214. Urethral sling 210 includes a widened central support portion and two load-transfer portions, one on each side of the central support portion. The load-transfer portions are "bi-arcuate" load transfer portions, meaning that each of the two load transfer portions includes two arcuate edges one extending in posterior and one extending in an anterior direction. Sutures 211 extend the length of implant 210, attached at attachment points 213, which may be knots, adhesive, or another mode of attachment.

Extension portions 212 include edges 216 extending at the location of a cut made in mesh 200, following heat-treatment to form heat-treated material 202. Each of edges 216 includes edge extensions 218 and reinforcement in the form of heat-treated material 202. FIG. 11C illustrates a close-up of edges 216, including mesh of extension portion 212, edge extensions 218 in the form of severed strand of un-heat-treated material, and heat-treated material 202 that includes a first row of fiber junctions (e.g., knots) 220 adjacent to edge extensions 218.

Still referring to FIG. 11C, the distance of the reinforcement of edge extensions 218, i.e., heat-treated material 202, from edge 216, can be any distance that stiffens edge extensions 218, and may depend on factors such as the type of mesh, size of connecting strands of mesh, size of knots, and length of edge extensions. For purposes of illustration, the two length-wise strips 202 located along each edge 216 may be at least 0.05 centimeter (measured laterally, perpendicular to the length of the edge) from the severed ends of edge extensions 518, e.g., from 0.1 centimeter from the severed ends of edge extensions 518.

A urethral sling can be installed as described herein with the assistance of surgical equipment, instruments, or tools that will be understood to be of assistance in performing the present surgical methods. Examples of surgical tools that may be useful include tools of the type described herein and in U.S. Pat. No. 6,911,003 and published US patent application No. 2003/0171644A1, which generally include right and left-handed opposing helical installation tools.

Exemplary surgical tools can comprise a needle sized and shaped to either a) initially extend through an incision substantially adjacent a patient's obturator foramen and then through the obturator foramen to a medial incision, or b) initially extend through a medial incision and subsequently through the obturator foramen and then to an incision substantially adjacent a patient's obturator foramen. Preferably, the needle comprises a pair of ends having surfaces for affording association with either an implantable sling material or a removable handle. In one embodiment, a needle is sized and shaped for use on either the patient's right side or left side (not both).

Embodiments of installation tools can include a substantially straight spacer portion emerging from an end of the handle portion preferably along a longitudinal axis of the handle. This helps afford convenient passage of the needle using an ergonomic wrist roll adopted by some surgeons.

A three-dimensional region of a needle can include a structure that can be described as a variable spiral or helix portion extending from the distal end of a straight spacer portion. A spiral portion can be variable as the angle of the spiral portion changes between the beginning of the spiral (e.g., the end of the spacer) and the distal end of the needle. The shape of the spiral portion can be designed to avoid over-insertion of the needle into the body, which helps avoid damage to the sensitive structures in this region of the body.

A useful needle can have dimension and shape features particularly useful in a male transobturator procedure, e.g., sufficient to extend from a lateral incision adjacent the anterior side of the pubic bone, through the obturator foramen portion of the pubic bone, to a position on the posterior side of the pubic bone, and to then emerge from a medial incision made between the patient's obturator foramen incisions. Alternate needles may be shaped to extend along the same tissue path in the opposite direction, entering at the medial incision and exiting at the lateral incision. A large number of different sizes, shapes, and dimensions of needles are suitable for the present invention.

In certain embodiments, a tool includes a handle or a portion of a handle may exhibit a non-circular form when viewed along the longitudinal axis of the handle. The non-circular cross-section can be, e.g., an oval, rectangle, rhombus, etc., having one dimension "width" that is greater than the dimension perpendicular to that "width." The non-circular form will provide surfaces on the handle for a surgeon to place pressure onto and to achieve a grip. The non-circular cross-sectional form also defines a midplane that is a plane that includes the longitudinal axis of the handle and extends along the widest dimension of the handle when viewed in cross section.

According to embodiments of the invention, a needle distal end of a tool (measured at the tip of the needle distal end) may be located at a position in space relative to the handle midplane and longitudinal axis, to provide the user with an ergonomic advantage. The ergonomic advantage may relate to useful or optimized (e.g., increased) amounts of force and control that can be applied at the needle distal end during the transobturator installation procedure, meaning amounts of force, sensitivity, and control that the user will have over the needle distal end when manipulating the handle using the midplane for leverage or grasping. As an example, a needle distal end may be located at an angle relative to the midplane to provide an ergonomic strength advantage or control advantage to a surgeon during particularly risky or sensitive portions of a surgical procedure, such as portions of a surgical procedure that involve using the needle distal end to dissect a tissue path through or near sensitive organs or tissues, e.g., traversing the obturator foramen. The angle between the needle distal end and the midplane may provide the surgeon with the use of maximum hand or wrist strength and maximum control and precision during manipulation of the needle distal end through a sensitive or risky tissue path, when applying pressure to a handle having a midplane. See Assignee's copending U.S. patent application Ser. No. 11/347,553, entitled "NEEDLE DESIGN FOR MALE TRANSOBTURATOR SLING," filed on even date herewith, the entirety of which is incorporated herein by reference.

FIGS. 12A and 12B illustrate two views of a tool useful according to the invention. FIG. 12A illustrates a view of tool 230 along a longitudinal axis of the tool. FIG. 12B illustrates a side view of tool 230. Tool 230 includes handle 232 and a needle extending longitudinally from an end of handle 232 along the longitudinal axis of the handle and tool. The needle includes spacer 234 and three-dimensional region 236 which may be considered to be a helix, a variable helix, or a spiral, etc. Diameter 238 can be larger than diameters of relevant prior art tools, and may be, for example, in the range from 2 to 5 centimeters, e.g., about 2.4 inches. Length 242 of spacer 234 can be any desired length, with an exemplary length 242 being in the range from 1 to 5 inches, e.g., from 1.75 to 2.25 inches. Length 240 of three-dimensional region 236 can be any desired length, such as in the range from 2.25 to 5 centimeters, e.g., from 2.4 to 2.5 inches. Angle y is approximately 45 degrees, and angle x is approximately 30 degrees, but may be otherwise, such as in the range from 20 to 70 degrees, or from 30 to 60 degrees. Needle end portion 244, which includes a length of about one inch at the end of the needle, is curved up until engaging portion 249, which is straight.

FIG. 12B shows an axis of needle end portion, line 252, or a plane defined by the needle end portion, that is substantially orthogonal to the longitudinal axis of handle 232. Distal end portion 244 can define either a line or a plane, depending on, e.g., whether the distal end portion is straight or curved. In FIG. 12A, distal end portion 244 includes a curve, and as such defines a plane including needle distal end 250. This plane, illustrated as line 252, is substantially orthogonal to the longitudinal axis of tool 30. Radial distance 251 of tool 230 can be as desired, e.g., in the range from about from 0.7 to 1.4 inches, e.g., from 0.9 to 1.1 inch for a male transobturator tool. Also shown at FIG. 12A, needle end portion 244, which includes a length of about one inch at the end of the needle, is curved up until engaging portion 249, which is straight.

In yet another aspect, the present invention comprises a surgical assembly or kit for treating incontinence. The assembly includes a urethral sling and two surgical instruments each having a handle portion, a needle portion having substantial structure in three dimensions, and a distal region. One surgical instrument comprises a handle portion and a needle portion having substantial structure in three dimensions and a distal region. The needle portion has a portion that is sized and shaped to extend between an incision substantially adjacent the obturator foramen on the patient's right side and a medial incision. The assembly also has a second surgical instrument for use on a left side of a patient. The second surgical instrument comprises a handle portion and a needle portion having substantial structure in three dimensions and a distal region. The needle portion of the second instrument has a portion that is sized and shaped to extend between an incision substantially adjacent the obturator foramen on the patient's left side and a medial incision.

Exemplary transobturator methods of installing a urethral sling include the steps of creating a medial incision at the external male perineum, creating two external opposing lateral incisions substantially adjacent the patient's left and right obturator foramen, and installing a urethral sling as described herein, end portions of which traverse the male obturator. The urethral sling may be placed using one or more tools as described, by installing end portions of the sling between the medial and the lateral incisions and passing through the obturator foramen. The end portion may be pushed through the tissue path at the leading edge of a needle, or may be pulled through the needle path using a trailing edge of the needle.

In more detail, an exemplary method includes steps of creating a medial incision at the exterior perineum, creating an external lateral incision substantially adjacent the patient's obturator foramen, providing an elongate surgical instrument comprising first and second regions, the instrument having substantial structure in three dimensions, and providing an implant for treating the incontinence (a urethral sling). The three-dimensional region of the needle may be passed between the incisions, and then the implant can be associated with the instrument, e.g., at the end of the three-dimensional region. For example, the needle may be passed from the lateral incision through the obturator foramen and to the medial incision, and the implant can be associated with the tip of the needle extending from the medial incision. The needle can then be pulled back through the incisions to pull the end portion of the implant from the medial incision, through the obturator foramen, and to the lateral incision.

Alternately, the implant can be associated with the needle before passing the needle between incisions. The needle, with the end portion of an implant associated with the needle tip, may then be passed between incisions, such as from the medial incision, through the obturator foramen, and then through the lateral incision. This can be done on both the right side and the left side.

In an alternate implantation method, a variation of a "transobturator" method (considered for the present description to be a "transobturator method") includes a method of inserting an implant through a medial, perineal incision and attaching an end portion of the implant to the obturator membrane. The anchor traverses or otherwise attaches to the obturator membrane. Other features of the inventive methods described herein can be incorporated into such a technique, such as placement of the urethral sling below the BC or CS, approximation of the urethra to improve continence (without the need for compression of the urethra), etc. This method avoids the need for lateral incisions.

In still another alternate embodiment of a transobturator method involving implantation using a needle with a three-dimensional region, single needle may be useful to place left and right end portions both left and right sides of a patient. A single left-handed needle (alternately a single right-handed needle) can be used to place a right side of the sling on a patient's right side, using a transobturator tissue path between a perineal incision and a patient's right-side lateral incision. In the same procedure, the same left-handed needle may also be used to place the opposite end portion on the patient's left side. While the left-handed needle is not optimal for placement at the patient's left side, it can be effective. Systems or kits of the invention can include a single left- or right-handed needle with an implant, for surgical implant according to this method.

Although the invention has been described in terms of particular embodiments and applications, one of ordinary skill, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

Exemplary Male Transobturator Sling System and Method

An exemplary sling system consists of two single-use surgical instruments called "needle passers" ("tool" or "needle") and a mesh implant with attached connectors, provided sterile. See FIG. 10. One end of each needle passer is keyed to allow for secure placement of the dilating connectors. Each needle passer has a plastic handle attached. The mesh is constructed of polypropylene monofilament that is precut to 1.2 centimeters arm width, 3.55 centimeters center width, and 35.5 centimeters length. Two absorbable tensioning sutures are threaded into the length of the sling system mesh to allow for tensioning adjustment of the sling system mesh after placement in the patient. Two plastic sheaths are placed over each arm of the sling system mesh to aid in ease of placement. The dilating connectors are attached to the ends of the needle passers during the procedure. The mesh is intended to remain in the body as a permanent implant and the mesh component is not absorbed or degraded by the action of tissue in-growth or tissue enzymes.

The system is intended for the placement of a pubourethral sling system for the treatment of male stress urinary incontinence (SUI) or intrinsic sphincter deficiency (ISD).

The procedure can be carried out under local, regional or general anesthesia. A small vertical incision is made in the area of the perineum followed by periurethral dissection. Two small stab incisions are also made above the obturator foramen for needle entry.

Preparation

1. Patient should be placed in a dorsal lithotomy position.
2. Genital area should be shaved.
3. After shaving, the area should be scrubbed with Povidone-iodine soap for ten minutes or the approved hospital pre-operative scrub procedure.
4. Ensure that the bladder is empty. A Foley catheter is not required but may aid in identifying the urethra during the procedure.

Dissection

1. The scrotum is elevated and a perineal incision is made, beginning midline at the level of the inferior edge of the symphysis and running approximately three centimeters toward the rectum.
2. The incision is carried deeper through Colles' fascia. The urethra is then mobilized by separating the bulbocavernosus muscle from the central tendon of the perineum.
3. The bulbocavernosus muscle is separated at the midline raphe and carefully dissected away from the corpus spongiosum.
4. A finger is placed between the bulbocavernosus muscle and the corpus spongiosum and with blunt dissection, the intersection of the corpus spongiosum and the perineal membrane is found.
5. The needle is inserted into the obturator foramen at a point bordering the inferior pubic ramus defining the foramen which lies approximately one-third of the distance below the forminal apex. Palpate the inferior pubic ramus and feel for the bony landmarks to locate the proper position. A needle through the skin can be used to probe the bone to help confirm that the correct location for the needle passer entry point is found, but it is not required. The position of entry is just below the medial aspect of the palpable part of the adductor longus tendon. The ideal position is at a point at the inner and medial aspect of the obturator foramen as high as possible to the foraminal apex.
6. Make small stab incisions at the correct location over both obturators (obturator foramina). Confirm that both marks lie in a straight line at the level shown in FIG. 6.
7. The patient is now ready for needle passage.

Passing the Insertion Needle Through the Obturator Foramen

1. Identify AMS Male Transobturator Sling System needle designated for the patient's left side.
2. Point the needle tip perpendicular to the skin and insert the needle into the patient's left stab incision previously made over the obturator foramen. The goal is to start with the needle tip hugging the medial aspect of the inferior pubic ramus within the obturator foramen at the level of the point one third below the cephalad peak of the obturator foramen.
3. Insert the needle to the level of the obturator fascia while hugging the bone with the needle tip.
4. Place an index finger in the perineal incision between the intersection of the corpus spongiosum and the perineal membrane on the side of the corpus spongiosum closest to the needle entry point.
5. When passing the needle on the patient's left side, keep the surgeon's right hand on the needle handle and left index finger in the perineal incision. The surgeon's left thumb should be on outside curve of needle to control the needle movement.

Figure 14:
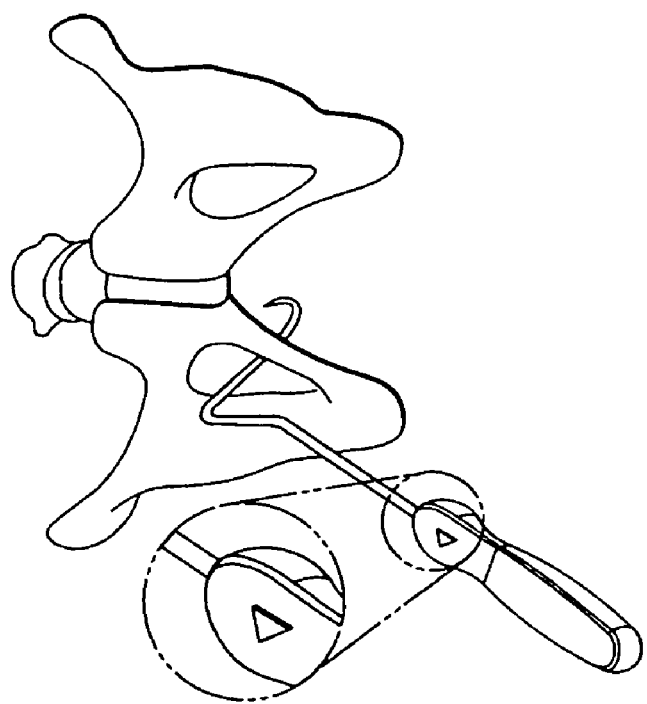
FIG. 14 illustrates an exemplary step of a surgical procedure as described.
Figure 13:
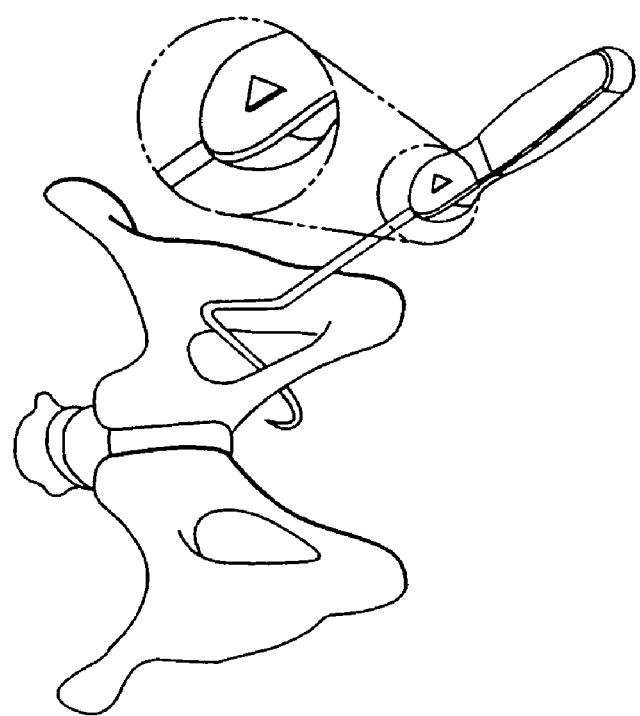
FIG. 13 illustrates an exemplary step of a surgical procedure as described.

See FIGS. 13 and 14.

6. Using the left thumb on the outside curve of the needle for to control needle movement, push the needle through the muscles and obturator fascia by turning the needle handle clockwise using the right hand. The needle tip penetrates until resistance of the tissue stops—about 0.5 centimeters.
7. Immediately locate the ischial pubic ramus with the needle tip and rotate the needle handle to allow the needle to follow the posterior ischial pubic ramus surface.
8. The index finger tip must palpate the needle tip while the needle is under the perineal membrane. The goal is to have the needle tip pass through the perineal membrane medial to the ischiocavernosus muscle, lateral to the corpus spongiosum and just below the level where the urethra passes through the perineal membrane. If not, move the needle to meet the finger tip. If the needle tip cannot be located, then the needle must be withdrawn just behind the ischial pubic ramus and carefully advanced again.
9. When the needle tip is in the correct position, guide the needle tip using the index finger through the perineal membrane until the needle extends through the incision.
10. Repeat the needle passage procedure (steps 2-9) on the patient's right side, with the needle designed for the right side.

Placing the Sling System Mesh

1. Attach the connectors (that are pre-attached to the AMS Sling System mesh) to the needle end. One connector should be attached to each of the needles on the end protruding from the perineal incision. Orient the knots of the tensioning sutures to be facing outward, away from the urethra. Be sure that the Sling System mesh lies flat and that the mesh is not twisted prior to attaching each connector.

2. Once both ends are connected, retract one needle along the same pathway, guiding with the fingertip.
3. Cut the insertion sheath and mesh at the external end of the plastic sheath and discard the needle, attached connector, sheath end, and mesh end. This step allows the sheath to slide freely relative to the mesh. Leave enough sheath material above the level of the skin so that the sheath can later be removed.
4. Repeat for the other needle on patient's contra lateral side to loosely position the Sling System with the tensioning sutures facing outward, away from the urethra. Loosely position the Sling System with the center of the central portion of the mesh sling approximately 1 centimeter distal to the line created between the needle passages on both sides of the corpus spongiosum.
5. In an optional step, before tensioning the sling, use two tack sutures to secure the placement of the sling to the midline of the corpus spongiosum. The sutures should be placed through the distal "flap" (anterior extension of the central support portion of the sling) just off of the center of the sling (at least two pores in from the edge of the sling mesh) and pass shallowly through the midline of the corpus spongiosum. When the sling is tensioned it will reposition the posterior urethral bulb approximately 1-4 centimeters proximal while elevating the perineal membrane.
6. The traction is parallel to the posterior urethra, which repositions the urethral lumen, rather than obstructing it.

Adjusting the Sling System Tension

1. If tissue retraction has been used, it must be removed before adjusting the tension of the Sling System. If a Foley catheter has been used, it must also be removed before adjusting the tension.
2. The AMS Male Transobturator Sling System mesh is properly tensioned by simultaneously pulling on the ends of the Sling System mesh and noticing approximately 1-4 centimeters proximal movement of the urethra.
3. If the patient is under spinal or regional anesthesia, the position of the AMS Male Transobturator Sling System can be verified by a cough test after filling the bladder, at the discretion of the surgeon.

To Loosen the Sling System Mesh:
  Place an instrument between the Sling System mesh and the urethra. Ensure that both the mesh and the tensioning sutures are located beneath the clamp. Use the clamp to pull down and loosen the Sling System mesh as desired.

To Tighten the Sling System Mesh:
  Clamp a device such as a hemostat, across the Sling System mesh, at the lateral incisions. Be sure that both the tensioning sutures and the complete width of the Sling System are captured within the clamp. The Sling System mesh may be rolled around the clamp to improve the grip. Pull up to tighten the Sling System mesh as desired. If needed, this can be repeated on the contra lateral side.

Remove the plastic sheath from the Sling System mesh and discard. Confirm the correct tension of the Sling System after the sheath has been removed.
Trim the Sling System mesh at the level of the subcutaneous tissue.
Complete a multi-layer closure of the perineal incision and the skin incisions.

Immediate Post-Operative Care
  A catheter can be used at the discretion of the surgeon.
  Antibiotic prophylaxis should be given.
  The ability of the patient to empty the bladder should be confirmed.

Example of Method of Preparation of Urethral Sling with Widened Central Support Portion and Reinforced Edge Extensions Exemplary urethral sling implants according to the invention were prepared according to the following, by the steps, in order, of (1) providing a sheet of mesh material, (2) heat treating the mesh to produce a heat treated area, and (3) cutting the heat treated mesh to form a urethral sling that includes reinforced edge extensions on end portions.

Step 1—Heat Treating or "Sealing" Mesh

A sheet of polypropylene knitted mesh was provided for treatment in a heat-treatment or heat-sealing machine. The mesh was of the type used in the MONARC™ and SPARC® female urethral slings used for treating female urinary incontinence, from American Medical Systems, Inc., of Minnetonka Minn. The mesh is that type that includes a "smooth" side and a "rough" side, as is known. The rough side may have a very slightly more rough feel compared to the smooth side; with reference to the direction of the loop that forms the weave, the loop points slightly more toward the "rough" side surface and slightly away from the "smooth" side surface. The "rough side" may be referred to as the "Technical Face" or "Loop Side" and the "smooth side" is called the "Technical Back" or "Lap Side". The invention can preferably apply heat ("sealing") at the Technical Back side of this type of mesh.

The pores are diamonds that have a size including an approximately 0.060" diameter measured (corner to corner) at the longer dimension and a 0.050" diameter measured in the shorter "width" direction (corner to corner). The sheet has rows of alternating diamonds that face up (the smallest angle point of the diamond faces up) adjacent to diamonds that face down (the smallest angle point of the diamond faces down). The machine was turned on and set machine to the following cycle parameters:

| | |
|---|---|
| Temp of heated sealing element: | 395° F. (±5° F.) |
| Pressure applied to mesh by sealing element | 35 psi (±5 psi) |
| Time of pressure application | 0.9 sec (±.1 sec) |

Figure 16:
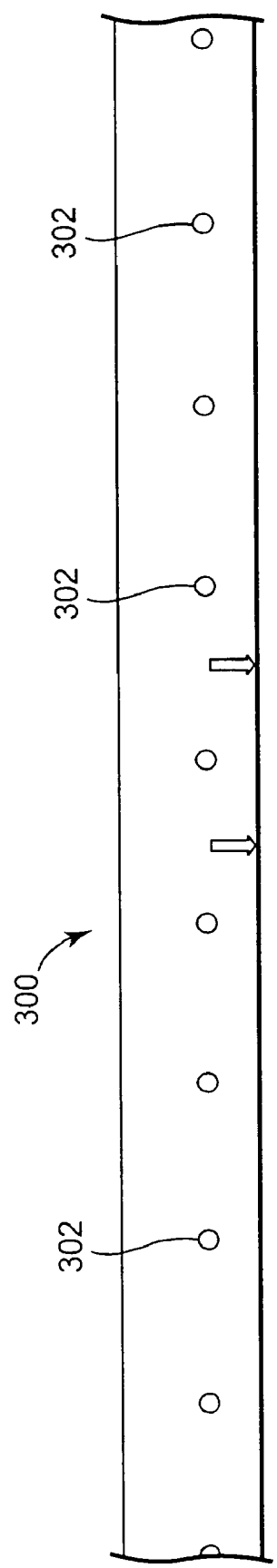
FIG. 16 illustrates exemplary equipment useful for preparing an implant.

The mesh was loaded rough-side-down onto a plate insert that includes a line of several pins that are inserted into the pores of the mesh. The plate insert fits into a groove for positioning the plate and mesh below a heat treating element and a cutting die, for heat treating and cutting at locations of the mesh to produce heat treated reinforcement adjacent to edges, i.e., reinforced edge extensions. A portion of a plate is shown at FIG. 16, which shows plate 300 and pins 302 (not to scale). Pins 302 are not at the center of the width of the plate but are located closer to one side (referred to as the "short side," and indicated with the arrow) than the other side. This is because of the asymmetry of the "diamond"-shaped pores used to prepare the urethral sling of the present example. The offset of the pins allows a cut of the mesh to align with pore openings as desired, and also allows heat sealing to align as desired, e.g., at a first junction of the mesh.

Figure 17:
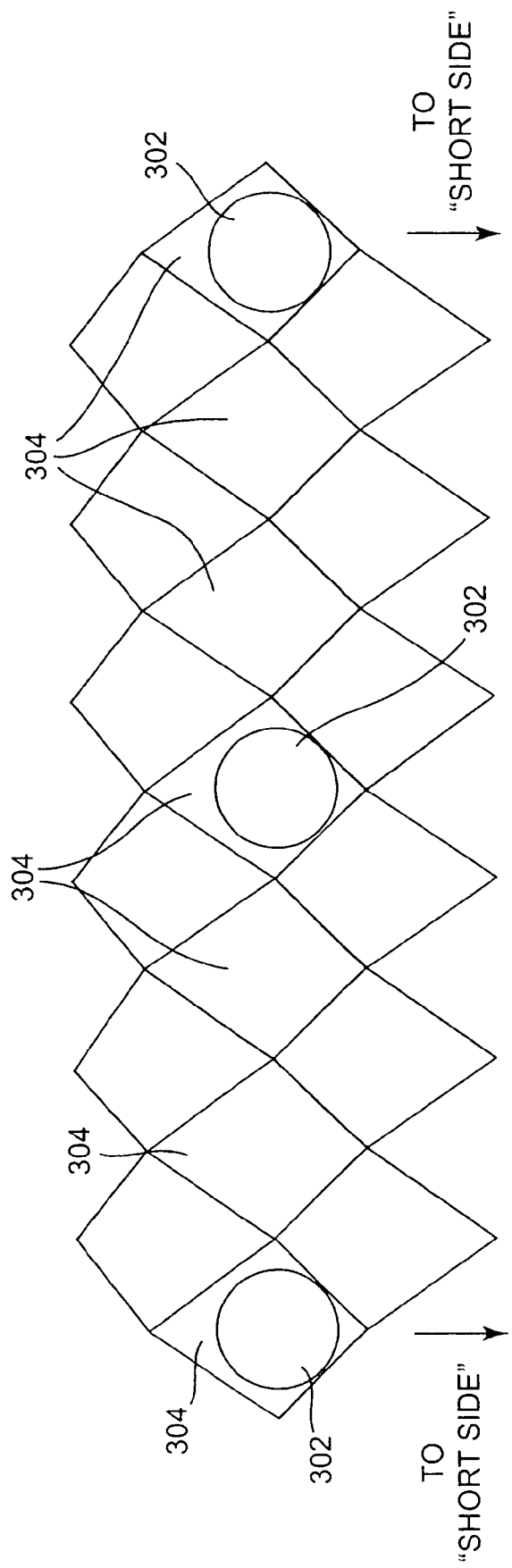
FIG. 17 illustrates an exemplary processing step of preparing an implant.

The mesh is aligned such that the pins of the plate are placed in the same row of pores of a mesh, with the pores being aligned along the length of the end portion as diamond-shapes as opposed to square-shapes (see FIG. 17). More specifically, because the diamonds of are asymmetrical, the diamonds are aligned with an orientation that points the smaller angle of the diamond in a direction away from the "short side" of the plate (indicated by arrows), i.e., the "diamond facing up" pores are held by pins 302. See FIG. 17, which schematically illustrates that pins 302 located to hold a single "row" of upward-facing diamonds 304, of with all diamonds held by pins 302 facing in the same direction.

A "mesh hold-down" piece is used to hold the mesh against the plate. The hold-down is made of Teflon and fits over the mesh and pins of the plate and does not otherwise interfere with the heating element contacting the mesh.

Load the mesh and plate into the heat seal machine, making sure the mesh is laying flat. Initiate heat treatment cycle with the parameters identified above.

Remove Mesh Hold-Down.

Step 2—Die Cutting the Sling

Figure 15:
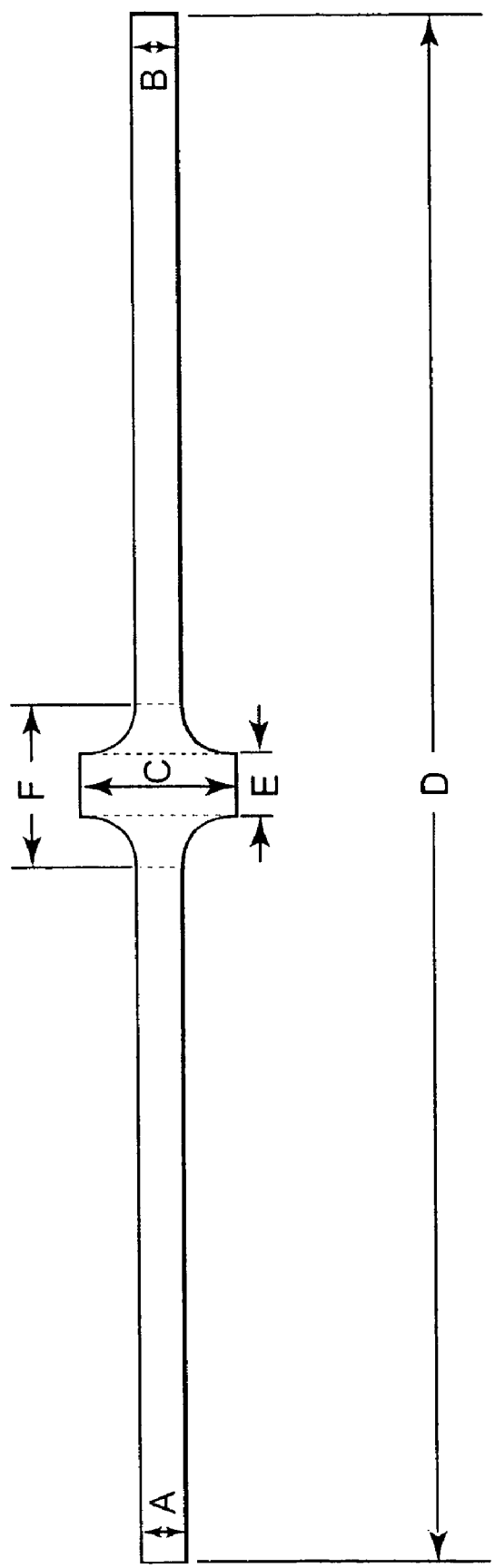
FIG. 15 illustrates exemplary equipment useful for preparing an implant.

A pneumatic press, cutting die, plate insert and attached mesh (above) are provided. The die includes a blade that is shaped like a one-piece urethral sling, with the following dimensions, as shown in FIG. 15.

| Dimension | Measured Value |
|---|---|
| A | 0.44" |
| B | 0.44" |
| C | 1.4" |
| D | 14" |
| E | 0.58" |
| F | 1.5" |

The pneumatic press is set to 55 psi (±5 psi).

The plate with the mesh on it is placed into the cutting die. This lines up the cut to be adjacent to the heat-treaded portion of the mesh.

The die and mesh are placed in to the pneumatic press and the stamping cover with the plastic side down is placed on to the die.

The press is activated to cut out the sling.

If any strands of the sling did not cut, a pair of scissors can be used to separate the sling from the mesh panel along the cutting line of the die.

If necessary, edges of the sling may be cleaned with a bristled brush to remove any loose sling material.

The invention claimed is:

1. A method of treating incontinence comprising the steps of:
    providing an elongate implantable sling comprising a central support portion and elongate end portions sized and shaped to extend between an incision substantially adjacent to a patient's obturator foramen, through the obturator foramen, and to a location below the urethra,
    creating a pair of lateral incisions substantially adjacent a patient's left and right obturator foramen,
    creating a medial incision at the perineum,
    exposing bulbospongiosus muscle,
    dissecting bulbospongiosus muscle to expose corpus spongiosum,
    placing the central support portion to contact the corpus spongiosum, and
    extending the end portions internally through the obturator foramen to the lateral incisions substantially adjacent to the obturator foramen.

2. The method of claim 1, comprising
    providing a left-hand surgical tool comprising a needle portion extending from a handle, the needle portion comprising a three-dimensional portion having structure in three dimensions and sized and shaped to extend between a patient's right-side lateral incision, through the obturator foramen, and to the medial incision,
    inserting a distal end of the left-hand tool through the right-side lateral incision, through a patient's right-side obturator foramen, and to the medial incision,
    associating an end of the sling with the distal end of the left-hand tool at the medial incision,
    drawing the end of the sling through the right-side obturator foramen to the right-side lateral incision,
    providing a right-hand surgical tool comprising a needle portion extending from a handle, the needle portion comprising a three-dimensional portion having structure in three dimensions and sized and shaped to extend between a patient's left-side lateral incision, through the obturator foramen, and to the medial incision,
    inserting a distal end of the right-hand tool through the left-side lateral incision, through a patient's left-side obturator foramen, and to the medial incision,
    associating an end of the sling with the distal end of the right-hand tool at the medial incision,
    drawing the end of the sling through the left-side obturator foramen to the left-side lateral incision.

3. The method of claim 1, comprising placing tension on the end portions of the sling to approximate pelvic tissue.

4. The method of claim 3, comprising approximating the urethra in a proximal direction.

5. The method of claim 3, comprising approximating the urethra in a proximal direction by a distance in the range from 1 to 5 centimeters.

6. The method of claim 1, comprising
    creating tissue paths between each lateral incision and the medial incision, exiting in the perineal region between the corpus cavernosum and the corpus spongiosus,
    placing the central support portion in contact with the corpus spongiosum at a location from 0.5 to 1.5 centimeters distal to a line created between needle passages on both sides of the corpus spongiosum, and
    placing tension on the end portions of the sling to approximate the corpus spongiosum.

7. The method of claim 1, wherein the patient is affected by a condition of perineal descent.

8. The method of claim 1, wherein the patient has experienced radical prostatectomy, a TURP (trans-urethral resection of the prostate), or a cystectomy.

9. The method of claim 1, wherein the approximating step repositions pelvic tissue to place a urethra to a more physiologically correct position to improve coaptation of the urethra by the rhabdosphincter.

10. The method of claim 1, wherein prior to the surgical procedure the patient exhibits residual sphincter function.

11. The method of claim 1, comprising
    contacting the central support portion to the corpus spongiosum, and
    after placement of the central support portion and the end portions, placing tension on the end portions of the sling to approximate tissue selected from the rhabdosphincter, the urethra, and a combination of these.

12. The method of claim 1, wherein the implant comprises a widened central support portion, and the method comprises placing the widened central support portion below the corpus spongiosum.

13. The method of claim 12, comprising securing the widened central support portion to the corpus spongiosum.

14. The method of claim 13, comprising securing the widened central support portion to the corpus spongiosum by use of a suture.

15. The method of claim 1 comprising treating incontinence in a male patient.

16. The method of claim 1 comprising approximating the urethra without placing compressive forces on the urethra.

17. The method of claim 1 comprising placing the central support portion in contact with the corpus spongiosum at a location below a membranous urethra.

18. The method of claim 1 comprising approximating pelvic tissue to improve coaptation of the urethra without requiring a compressive effect on the urethra.

19. The method of claim 1 comprising
treating incontinence in a male patient,
approximating pelvic tissue without requiring a compressive effect on the urethra, and
placing the central support portion in contact with the corpus spongiosum at a location below a membranous urethra.

20. The method of claim 1 comprising associating an end portion of the implant with a needle and passing the needle between the medial incision and a lateral incision by inserting the needle at the medial incision, passing the needle through an obturator foramen, and then passing the needle through the lateral incision.

21. The method of claim 1 comprising associating a first end portion of the implant with a first needle and passing the first needle between the medial incision and a right-side lateral incision by inserting the first needle at the medial incision, passing the first needle through the right-side obturator foramen, and then passing the first needle through the right-side lateral incision, and
associating a second end portion of the implant with a second needle and passing the second needle between the medial incision and a left-side lateral incision by inserting the second needle at the medial incision, passing the second needle through the left-side obturator foramen, and then passing the second needle through the left-side lateral incision.

22. The method of claim 1 comprising using a finger passed between the bulbocavernous muscle and the corpus spongiosum, to identify the intersection of the corpus spongiosum and the perineal membrane.

23. The method of claim 1 comprising passing a needle tip through a pernineal membrane of the patient, lateral to the corpus spongiosum.

24. A method of treating incontinence in a male patient, the method comprising
providing an elongate implantable sling comprising a central support portion and elongate end portions,
creating an incision at the perineum of the male patient,
exposing bulbospongiosus muscle,
dissecting the bulbospongiosus muscle to expose corpus spongiosum,
inserting the implant through the perineal incision,
installing the central support portion below the bulbous urethra to contact the corpus spongiosum, and
attaching an end portion to an obturator membrane without making a lateral incision substantially adjacent the patient's obturator foramen.

25. The method of claim 24, comprising placing tension on the sling to approximate pelvic tissue including the urethra, to improve sphincter function and coaptation of the urethra.

26. The method of claim 24 wherein the implant comprises a widened central support portion, and the method comprises placing the widened central support portion below the corpus spongiosum.

27. The method of claim 24 comprising approximating the urethra without placing compressive forces on the urethra.

28. The method of claim 24 comprising placing the central support portion at a location below a membranous urethra.

29. The method of claim 24 comprising approximating pelvic tissue to improve coaptation of the urethra without requiring a compressive effect on the urethra.

30. The method of claim 24 comprising
treating incontinence in a male patient,
approximating pelvic tissue without requiring a compressive effect on the urethra, and
placing the central support portion at a location below a membranous urethra.

31. The method of claim 24 wherein the implant comprises an anchor and the anchor attaches to the obturator membrane.

* * * * *

UNITED STATES PATENT AND TRADEMARK OFFICE
CERTIFICATE OF CORRECTION

| | | |
|---|---|---|
| PATENT NO. | : 7,914,437 B2 | Page 1 of 1 |
| APPLICATION NO. | : 11/347047 | |
| DATED | : March 29, 2011 | |
| INVENTOR(S) | : Christian Gozzi et al. | |

It is certified that error appears in the above-identified patent and that said Letters Patent is hereby corrected as shown below:

Column 5, line 13, "increase" should be -- increases --.
Column 7, line 15, "preferably maintained" should be -- preferably be maintained --.
Column 8, line 50, "may mis-positioned" should be -- may be mis-positioned --.
Column 12, line 67, delete "with".
Column 20, line 33, after "on" add -- the --; after "of" add -- the --.
Column 20, line 36, delete "for".
Column 23, line 1, delete "of" (second occurrence).

Signed and Sealed this
Seventeenth Day of May, 2011

David J. Kappos
*Director of the United States Patent and Trademark Office*